United States Patent
Burgey et al.

(10) Patent No.: US 10,004,740 B2
(45) Date of Patent: *Jun. 26, 2018

(54) PRODRUGS OF HIV REVERSE TRANSCRIPTASE INHIBITORS

(71) Applicant: Merck Sharp & Dohme Corp., Rahway, NJ (US)

(72) Inventors: Christopher S. Burgey, Ambler, PA (US); Jeffrey F. Fritzen, Pottstown, PA (US); Jaume Balsells, North Wales, PA (US); Mehul Patel, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/300,405

(22) PCT Filed: Mar. 27, 2015

(86) PCT No.: PCT/US2015/022868
§ 371 (c)(1),
(2) Date: Sep. 29, 2016

(87) PCT Pub. No.: WO2015/153304
PCT Pub. Date: Oct. 8, 2015

(65) Prior Publication Data
US 2017/0173015 A1    Jun. 22, 2017

Related U.S. Application Data

(60) Provisional application No. 61/973,689, filed on Apr. 1, 2014.

(51) Int. Cl.
| | | |
|---|---|---|
| *C07D 403/06* | (2006.01) | |
| *C07D 237/22* | (2006.01) | |
| *C07D 239/47* | (2006.01) | |
| *A61K 31/501* | (2006.01) | |
| *A61K 31/506* | (2006.01) | |
| *A61K 31/513* | (2006.01) | |
| *A61P 31/18* | (2006.01) | |
| *A61K 45/06* | (2006.01) | |

(52) U.S. Cl.
CPC .......... *A61K 31/506* (2013.01); *A61K 31/501* (2013.01); *A61K 31/513* (2013.01); *A61K 45/06* (2013.01); *C07D 237/22* (2013.01); *C07D 239/47* (2013.01); *C07D 403/06* (2013.01)

(58) Field of Classification Search
CPC ... A61K 31/501; A61K 31/506; C07D 403/06
USPC .............. 544/238, 295; 514/252.02
See application file for complete search history.

(56) References Cited

U.S. PATENT DOCUMENTS

| | | | |
|---|---|---|---|
| 5,519,021 A | 5/1996 | Young et al. | |
| 7,166,738 B2 | 1/2007 | Dunn et al. | |
| 7,189,718 B2 | 3/2007 | Dunn et al. | |
| 7,288,942 B2 * | 10/2007 | Zhang | G01N 27/62 324/464 |
| 8,486,975 B2 | 7/2013 | Burch et al. | |
| 9,469,634 B2 * | 10/2016 | Han | C07D 401/14 |
| 2004/0192704 A1 | 9/2004 | Dunn et al. | |
| 2005/0065145 A1 | 3/2005 | Cao et al. | |
| 2005/0215554 A1 | 9/2005 | Dunn et al. | |
| 2007/0021442 A1 | 1/2007 | Saggar et al. | |
| 2008/0207654 A1 | 8/2008 | Kuroita et al. | |
| 2009/0176812 A1 | 7/2009 | Kuroita et al. | |
| 2011/0245296 A1 | 10/2011 | Burch et al. | |
| 2013/0040914 A1 * | 2/2013 | Jolly | C07F 9/6561 514/81 |

(Continued)

FOREIGN PATENT DOCUMENTS

| | | |
|---|---|---|
| WO | 2000003998 A1 | 1/2000 |
| WO | 2001034578 A1 | 5/2001 |
| WO | 2004069812 A1 | 1/2004 |

(Continued)

OTHER PUBLICATIONS

Sultan et al. HIV/AIDS—Research and Palliative Care 2014:6 147-158.*
Freshney et al.,Culture of Animal Cells, A Manual of Basic Technique, Alan R. Liss, Inc., 1983, New York, p. 4.*
Dermeret al., Bio/Technology, 1994, 12:320.*
Clemo, G.R., et al, "The Lupin Alkaloids. Part XV. Some Derivatives of the 4-Oxo-3-2'-Pyridylpyridocoline System", J. Chem. Soc., 1954, pp. 2693-2702, vol. 00, No. 00.

(Continued)

*Primary Examiner* — Venkataraman Balasubramanian
(74) *Attorney, Agent, or Firm* — Carol S. Quagliato; John C. Todaro

(57) ABSTRACT

Compounds of Formula I are described: wherein $R^1$ and $R^2$ are defined herein. The compounds of Formula I are useful in the inhibition of HIV reverse transcriptase, the prophylaxis and treatment of infection by HIV, and the prophylaxis, delay in the onset or progression, and treatment of AIDS. The compounds can be employed as ingredients in pharmaceutical compositions, optionally in combination with other antivirals, immunomodulators, antibiotics or vaccines.

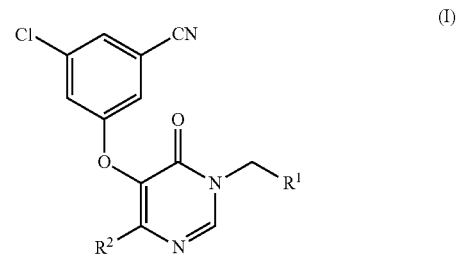

(I)

32 Claims, No Drawings

(56) References Cited

U.S. PATENT DOCUMENTS

2013/0296382 A1 11/2013 Burch et al.
2014/0100231 A1* 4/2014 Arrington ............ C07D 401/14
 514/248

FOREIGN PATENT DOCUMENTS

| WO | 2004074257 A1 | 9/2004 |
| --- | --- | --- |
| WO | 2004085406 A2 | 10/2004 |
| WO | 2005070901 A2 | 8/2005 |
| WO | 2005102989 A1 | 11/2005 |
| WO | 2006067587 A1 | 6/2006 |
| WO | 2007015812 A2 | 2/2007 |
| WO | 2007045572 A1 | 4/2007 |
| WO | 2007045573 A1 | 4/2007 |
| WO | 2008076225 A1 | 6/2008 |
| WO | 2009067166 A2 | 5/2009 |
| WO | 2008085406 A2 | 9/2010 |
| WO | 2011120133 A1 | 10/2011 |
| WO | 2011126969 A1 | 10/2011 |
| WO | 2014058747 A1 | 4/2014 |
| WO | 2015153304 A1 | 10/2015 |

OTHER PUBLICATIONS

Ji, L., et al,, "Synthesis and Anti-HIV-1 Activity evaluation of 5-alkyl-2-alkylthio-6-(Arylcarbonyl or a-Cyanoarylmethyl)-3,4-Dihydropyrimidin-4(3H)-Ones As Novel Non-Nucleoside HIV-1 Reverse Transcriptase Inhibitors", Journal of Medicinal Chemistry, 2007, pp. 1778-1786, vol. 50.

Li, A., et al,, "Novel Pyridinone Derivativese As Non-Nucleoside Reverse Transcriptase Inhibitors (NNRTIs) with High Potency Against NNRTI-Resistant HIV-1 Strains", Journal of Medicinal Chemistry, 2013, pp. 3593-3608, vol. 56.

Sweeney, Z.K., et al, "Discovery of Triazolinone Non-Nucleoside Inhibitors of HIV Reverse Transcriptase", Bioorganic & Medicinal Chemistry Letters, Aug. 1, 2008, pp. 4348-4351, vol. 18, No. 15.

Beaumont, K., et al,, "Design of Ester Prodrugs to Enhance Oral Absorption of Poorly Permeable Compounds: Challenges to the Discovery Scientist", Current Drug Metabolism, 2003, pp. 461-485, vol. 4.

Butters, M., et al,, "Process Development of Voriconazole: A Novel Broad-Spectrum Triazole Antifungal Agent", Org. Proc. Res. & Dev., 2001, pp. 28-36, vol. 5.

European Searching Authority—EP Search Report—EP Application No. 15 77 4282.

Hale, et al, Phosphorylated Morpholine Acetal Human Neurokinin-1 Receptor Antagonists As Water-Soluble Prodrugs, J. Med. Chem, 2000, 1234-1241, vol. 43.

International Searching Authority Written Opinion—PCT/US2013/063612—International Filing Date: Oct. 7, 2013.

International Searching Authority Written Opinion—PCT/US2015/22868—International Filing Date: Mar. 27, 2015.

Kesisoglou, F., et al, "Nanosizing—Oral Formulation Development and Biopharmaceutical Evaluation", Advanced Drug Delivery Reviews, 2007, pp. 631-644, vol. 59, US.

Larrsen, C.S., et al,, "Design and Application of Prodrugs", Textbook of Drug Design and Discovery, 3rd ED, 2002, pp. 410-458, Chapter 14, US.

Radi, M., et al "Discovery of Chiral Cyclopropyl Dihydro-Alkylthio-Benzyl-Oxopyrimidine (S-DABO) Derivatives As Potent HIV-1 Reverse Transcriptase Inhibitors With High Activity Against Clinically Relevant Mutants", J. Med. Chem., 2009, pp. 840-851, vol. 52, American Chemical Society, US.

Serajuddin, A., et al,, "Solid Dispersion of Poorly Water-Soluble Drugs: Early Promises, Subsequent Problems, and Recent Breakthroughs", J. Pharm Sci., 1999, pp. 1058-1066, vol. 88, No. 10.

Thenappan, A., et al,, "An Expedient Synthesis of a-Fluoro-b-Ketoesters", Tetrahedron Letters, 1989, pp. 6113-6116, vol. 30, No. 45.

International Searching Authority—PCT Search Report—PCT/US2015/22868.

* cited by examiner

PRODRUGS OF HIV REVERSE TRANSCRIPTASE INHIBITORS

RELATED APPLICATIONS

This application is a 35 U.S.C. § 371 filing from International Application No. PCT/US2015/022868, filed Mar. 27, 2015, which claims priority to U.S. Provisional Application No. 61/973,689, filed Apr. 1, 2014. Each of the aforementioned applications to which this application claims priority is herein incorporated by reference in its entirety.

The sequence listing of the present application is submitted electronically via EFS-Web as an ASCII formatted sequence listing with a file name "23744-US-PSP-SE-QLIST-01APR2014", having a creation date of Apr. 1, 2014, and a size of 1.92 kb. This sequence listing submitted via EFS-Web is part of the specification and is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz, abacavir, emtricitabine, and tenofovir. Current standard of care is to employ highly active anti-retroviral therapy (HAART). HAART therapy is defined as the combination of 3 agents from at least 2 different mechanistic classes. While HAART based treatment regimens employing RT inhibitors are effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to treat HIV infection will inevitably result in the emergence of new resistant strains of HIV. Accordingly, there is a particular need for new RT inhibitors that are effective against mutant HIV strains.

WO 2009/067166 and WO 2011/126969 disclose certain RT inhibitors prodrugs. Clemo et al., *J. Chem. Soc.* 1954, pp. 2693-2702 discloses certain derivatives of the 4-oxo-3-(2-pyridyl)pyridocoline system and in particular discloses 6-methyl-6'-phenoxy-2,2'-methylenedipyridine. Sweeney et al., *Bioorganic & Medicinal Chem. Letters* 2008, vol. 18, pp. 4348-4351 discloses a series of triazolinones that were found to be non-nucleoside inhibitors of HIV reverse transcriptase. WO 2001/034578 discloses certain substituted azoles (including, for example, certain imidazoles and benzimidazoles) having anti-*Helicobacter pylori* activity. In particular, WO '578 discloses 1-[(3-methyl-4-phenoxy-2-pyridinyl)methyl]-1H-benzimidazole (see Compound 91 on page 40). WO 2004/085406 and corresponding U.S. Pat. No. 7,189,718 disclose certain benzyl pyridazinones as reverse transcriptase inhibitors. WO 2005/102989 and corresponding U.S. Pat. No. 7,166,738 disclose certain N-phenyl 2-phenylacetamides to be non-nucleoside reverse transcriptase inhibitors. WO 2006/067587 discloses certain biaryl ether derivatives to be modulators of the reverse transcriptase enzyme. WO 2007/045572 and WO 2007/045573 disclose certain 2-(2-phenoxyphenyl) N-phenyl acetamides as non-nucleoside reverse transcriptase inhibitors. WO 2008/076225 discloses certain indazoles, benzotriazoles and related bicyclic compounds as HIV reverse transcriptase inhibitors. WO 2009/067166 discloses certain aryloxy-, cycloalkyloxy-, and heterocyclyloxy-pyridines and related compounds. The compounds are HIV reverse transcriptase inhibitors suitable, for example, for the treatment of infection by HIV. Among the compounds disclosed are certain 3-(3,5-disubstituted phenoxy)-1-(1H-pyrazolo[3,4-b]pyridin-3-ylmethyl)-4-(substituted)pyridin-2(1H)-ones. US 2004/0192704 discloses certain 3-(phenoxy)benzyl substituted 5-membered triazolones, oxadiazolones, and thiadiazolones. The compounds are disclosed to be non-nucleoside reverse transcriptase inhibitors useful for the treatment or prophylaxis of HIV mediated diseases. US 2007/0021442 and WO 2007/015812 disclose certain substituted aromatic compounds. The compounds are HIV reverse transcriptase inhibitors suitable, for example, for the treatment of infection by HIV. WO 2009/067166 and WO2011/120133 discloses HIV non-nucleoside reverse transcriptase inhibitors. WO 2011/126969 discloses prodrugs of HIV non-nucleoside reverse transcriptase inhibitors

SUMMARY OF THE INVENTION

The present invention is directed to certain derivatives of 4-pyrimidinones. The compounds of Formula I are believed to be pro-drugs which can be metabolized in vivo to compounds of Formula I' (defined below) which are inhibitors of HIV reverse transcriptase. The compounds of Formula I' inhibit the polymerase function of HIV-1 reverse transcriptase, and more particularly inhibit the RNA-dependent DNA polymerase activity of HIV-1 reverse transcriptase. The compounds of Formula I' also exhibit activity against drug resistant forms of HIV (e.g., mutant strains of HIV-1 in which reverse transcriptase has a mutation at lysine 103→asparagine (K103N) and/or tyrosine 181→cysteine (Y181C)). Thus compounds of Formula I, which can be used to facilitate administration of compounds of Formula I', can exhibit decreased cross-resistance against currently approved antiviral therapies. Therefore, the compounds of Formula I (including hydrates and solvates thereof) are useful, for example, in the inhibition of HIV reverse transcriptase, the prophylaxis of infection by HIV, the treatment of infection by HIV and in the prophylaxis, treatment, and delay in the onset or progression of AIDS and/or ARC, either as compounds per se, or as pharmaceutical composition ingredients, whether or not in combination with other HIV antivirals, anti-infectives, immunomodulators, antibiotics or vaccines.

DETAILED DESCRIPTION OF THE INVENTION

The invention encompasses compounds of structural Formula I or a pharmaceutically acceptable salt thereof:

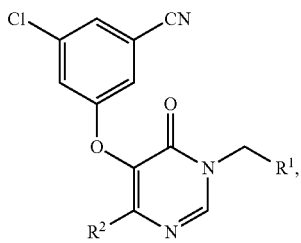

I wherein $R^1$ is

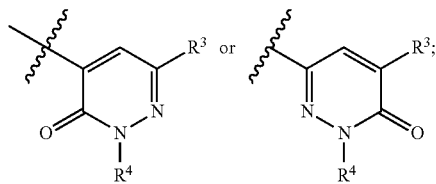

$R^2$ is halo or —$C_{1-3}$ alkyl substituted with 1 to 3 of —F;
$R^3$ is (a) halo, (b) —$C_{1-3}$ alkyl substituted with 1 to 3 of —F, or (3) phenyl substituted with halo; and
$R^4$ is

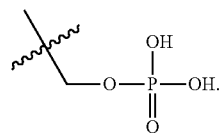 [SMILES: *COP(=O)(O)O]

In Embodiment A of this invention are compounds of Formula I or a pharmaceutically acceptable salt thereof wherein $R^1$ is

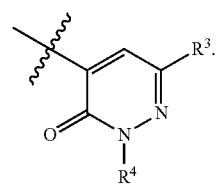

In Embodiment B of this invention are compounds of Formula I or a pharmaceutically acceptable salt thereof wherein $R^1$ is

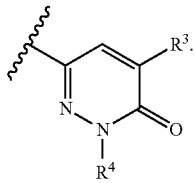

In another embodiment of this invention are compounds of Formula I or Embodiment A or Embodiment B, or a pharmaceutically acceptable salt thereof, wherein $R^2$ is methyl substituted with 1, 2 or 3 of —F; or ethyl substituted with 1, 2 or 3 of —F; and more particularly $R^2$ is —$CHF_2$, —$CF_3$, or —$CF_2CH_3$.

In another embodiment of this invention are compounds of Formula I or Embodiment A or Embodiment B, or a pharmaceutically acceptable salt thereof, wherein $R^3$ is —F; —Cl; methyl substituted with 1, 2 or 3 of —F; ethyl substituted with 1, 2 or 3 of —F; or phenyl substituted with —F; and more particularly $R^3$ is —Cl, —$CHF_2$, —$CF_3$, —$CF_2CH_3$, or phenyl substituted with —F.

In another embodiment of this invention are compounds of Formula I, Embodiment A or Embodiment B, or a pharmaceutically acceptable salt thereof, wherein:

$R^2$ is methyl substituted with 1, 2 or 3 of —F; or ethyl substituted with 1, 2 or 3 of —F; and more particularly $R^2$ is —$CHF_2$, —$CF_3$, or —$CF_2CH_3$;

$R^3$ is —F, —Cl, methyl substituted with 1, 2 or 3 of —F; ethyl substituted with 1, 2 or 3 of —F; or phenyl substituted with —F; and more particularly $R^3$ is —Cl, —$CHF_2$, —$CF_3$, —$CF_2CH_3$, or phenyl substituted with —F; and $R^4$ is

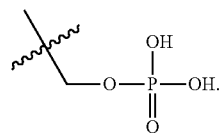 [SMILES: *COP(=O)(O)O]

As used herein, the term "alkyl" refers to a straight or branched chain, saturated aliphatic hydrocarbon radical having a number of carbon atoms in the specified range. Thus, for example, "—$C_{1-3}$ alkyl" means linear or branched chain alkyl groups, including all isomers, having the specified number of carbon atoms, i.e., n- and i-propyl (Pr=propyl), ethyl (Et) and methyl (Me).

The term "halogen" (or "halo") refers to fluorine, chlorine, bromine or iodine (alternatively referred to as fluoro, chloro, bromo, and iodo). Fluoro or chloro are preferred.

The compounds of Formula I are believed to act as pro-drugs which are converted in vivo into their pharmaceutically active counterparts of Formula I', wherein Formula I' is identical to Formula I except that $R^4$ is replaced with —H. For a specific compound of Formula I, the corresponding compound of Formula I' may be referred to herein as the "Parent" compound (whether or not either or both of the corresponding compounds are in a salt form, unless specified otherwise), e.g.,

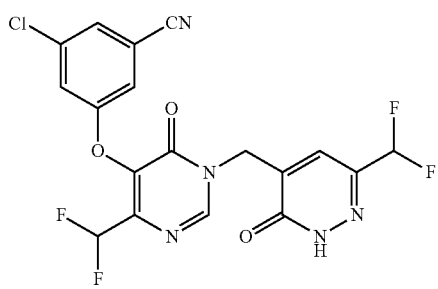 [SMILES: N#Cc1cc(Cl)cc(Oc2c(C(F)F)ccn(Cc3cc(C(F)F)n[nH]c3=O)c2=O)c1]

Parent compound of Example 1
(within scope of Formula 1')

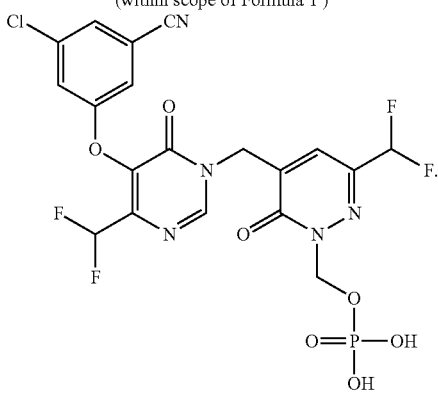

Example 1
(within scope of Formula 1)

The compounds of Formula I' are HIV reverse transcriptase inhibitors. Rat AUC data for the compounds of Examples 1-8 are provided in Table 3, infra.

All structural Formulas, embodiments and classes thereof described herein include the pharmaceutically acceptable salts of the compounds defined therein. Reference to the compounds of Formula I herein encompasses the compounds of Formulas I and all embodiments and classes thereof. Reference to the compounds of this invention as those of a specific formula or embodiment, e.g., Formula I, or embodiments thereof, or any other generic structural formula or specific compound described or claimed herein, is intended to encompass the specific compound or compounds falling within the scope of the Formula or embodiment, including salts thereof, particularly pharmaceutically acceptable salts, solvates (including hydrates) of such compounds and solvated salt forms thereof, where such forms are possible, unless specified otherwise The present invention includes each of the Examples described herein, and pharmaceutically acceptable salts thereof. The invention also encompasses pharmaceutical compositions comprising an effective amount of a compound of the invention or a pharmaceutically acceptable salt thereof, and a pharmaceutically acceptable carrier.

Unless expressly stated to the contrary, substitution by a named substituent is permitted on any atom in a chain or ring provided such substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I and its embodiments.

To the extent substituents and substituent patterns provide for the existence of tautomers (e.g., keto-enol tautomers) in the compounds of the invention, all tautomeric forms of these compounds, whether present individually or in mixtures, are within the scope of the present invention. It is understood that a reference to a compound capable of tautomerism includes within its scope a reference to each individual tautomer and combinations thereof, e.g., keto and enol forms.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

The compounds can be administered in the form of pharmaceutically acceptable salts. The term "pharmaceutically acceptable salt" refers to a salt which is not biologically or otherwise undesirable (e.g., is neither toxic nor otherwise deleterious to the recipient thereof). When the compounds of Formula I contain one or more acidic or basic groups the invention also includes the corresponding pharmaceutically acceptable salts. Thus, the compounds of Formula I which contain acidic groups can be used according to the invention as, for example but not limited to, alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamidic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, pharmaceutically acceptable inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of pharmaceutically acceptable salts.

As an example, the compounds of Formula I include, but are not limited to, such compounds wherein the alkylphosphate of $R^4$ may be a base salt, which refers to a pharmaceutically acceptable salt which is represented by the loss of at least one proton from the group balanced by one or more positive counter-ions (e.g., an alkali metal cation). A base salt of $R^4$ can be represented as:

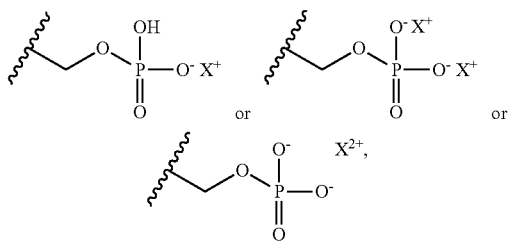

wherein $X^+$ and $X^{2+}$ are positive counter-ions. The base salt can be formed by treating the free form of the compound of Formula I with a suitable inorganic or organic base. Suitable inorganic bases include but are not limited to ammonium hydroxide, alkali metal hydroxides (e.g., NaOH or KOH), alkaline earth metal hydroxides and the like. Suitable organic bases include alkali metal alkylcarboxylates (e.g., potassium acetate or sodium acetate), alkyl ammonium hydroxides and the like.

Another embodiment of the present invention is a compound of Formula I wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, compounds of the instant invention may form solvates with water (i.e., a hydrate) or common organic solvents. The solvates include both stoichiometric and non-stoichiometric solvates. Such solvates and hydrates, particularly the pharmaceutically acceptable solvates and hydrates, of the instant compounds are likewise encompassed within the scope of this invention, along with un-solvated and anhydrous forms.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, where such forms are possible unless specified otherwise.

The invention also encompasses methods for the treatment or prophylaxis of infection by HIV, for the inhibition of HIV reverse transcriptase, or for the treatment, prophylaxis, or delay in the onset of AIDS in a subject in need thereof, which comprises administering to the subject an effective amount of a compound of the invention or a pharmaceutically acceptable salt thereof.

The invention also encompasses a compound of the invention, or a pharmaceutically acceptable salt thereof, for use in the preparation of a medicament for the treatment or prophylaxis of infection by HIV, for the inhibition of HIV reverse transcriptase, or for the treatment, prophylaxis, or delay in the onset of AIDS in a subject in need thereof.

The invention also encompasses a pharmaceutical composition comprising an effective amount of a compound of the invention, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents. Within this embodiment, the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

Other embodiments of the present invention include the following:

(a) A pharmaceutical composition comprising an effective amount of a compound of Formula I or Embodiment A or B as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I or Embodiment A or B as defined above, or a prodrug or pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(e) A combination which is (i) a compound of Formula I or Embodiment A or B as defined above, or a prodrug or pharmaceutically acceptable salt thereof, and (ii) an anti-HIV agent selected from the group consisting of HIV antiviral agents, immunomodulators, and anti-infective agents; wherein the compound and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, nucleoside HIV reverse transcriptase inhibitors, non-nucleoside HIV reverse transcriptase inhibitors, HIV integrase inhibitors, HIV fusion inhibitors, and HIV entry inhibitors.

(g) A method for the inhibition of HIV reverse transcriptase in a subject in need thereof which comprises administering to the subject an effective amount of a compound of Formula I or Embodiment A or B or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or Embodiment A or B or a prodrug or pharmaceutically acceptable salt thereof.

(i) The method of (h), wherein the compound of Formula I or Embodiment A or B is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(j) A method for the prophylaxis, treatment or delay in the onset or progression of AIDS in a subject in need thereof which comprises administering to the subject an effective amount of a compound of Formula I or Embodiment A or B or a prodrug or pharmaceutically acceptable salt thereof.

(k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I or Embodiment A or B, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, aspects, classes, sub-classes, or features described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors.

Unless expressly stated to the contrary, all ranges cited herein are inclusive. It is also understood that any range cited herein includes within its scope all of the sub-ranges within that range. For example, a moiety described as optionally substituted with "from 1 to 3 substituents" is intended to include as aspects thereof, such moiety substituted with 1 to 3 substituents, 2 or 3 substituents, 3 substituents, 1 or 2 substituents, 2 substituents, or 1 substituent. As another example, a dosage in a range of 1 to 500 milligrams means the dosage can be 1 mg or 500 mg or any amount therebetween.

The methods of the present invention involve the use of compounds of the present invention in the inhibition of HIV reverse transcriptase (e.g., wild type HIV-1 and other strains), the prophylaxis or treatment of infection by HIV and the prophylaxis, treatment or delay in the onset or progression of consequent pathological conditions such as AIDS. Preventing AIDS, treating AIDS, delaying the onset or progression of AIDS, or treating or preventing infection by HIV is defined as including, but not limited to, treatment of a wide range of states of HIV infection: AIDS, ARC, both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery. As another example, the present invention can also be employed to inhibit transmission of HIV from a pregnant female infected with HIV to her unborn child or from an HIV-infected female who is nursing (i.e., breast feeding) a child to the child via administration of an effective amount of a compound of Formula I.

The term "administration" and variants thereof (e.g., "administering" a compound) in reference to a compound of Formula I means providing the compound to the individual in need of treatment or prophylaxis and includes both self-administration and administration to the patient by another person. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" or "patient" as used herein refers to an animal, preferably a mammal, most preferably a human, who has been the object of treatment, observation or experiment.

The term "effective amount" as used herein means an amount sufficient to inhibit HIV reverse transcriptase, inhibit HIV replication, exert a prophylactic effect, and/or a exert a therapeutic effect after administration. One embodiment of "effective amount" is a "therapeutically effective amount" which is an amount of a compound that is effective for inhibiting HIV replication (which may also be referred to herein as an "inhibition effective amount"), treating HIV infection, treating AIDS, delaying the onset of AIDS, and/or slowing progression of AIDS in a patient. Another embodiment of "effective amount" is a "prophylactically effective amount" which is an amount of the compound that is effective for prophylaxis of HIV infection or prophylaxis of AIDS in a patient. It is understood that an effective amount can simultaneously be both a therapeutically effective amount, e.g., for treatment of HIV infection, and a prophylactically effective amount, e.g., for prevention or reduction of risk for developing AIDS. When the compound of Formula I is administered as a salt, reference to an amount of the compound is to the free form (i.e., the non-salt form) of the compound.

In the methods of the present invention (e.g., inhibiting HIV reverse transcriptase, treating or prophylaxis of HIV infection, inhibiting HIV replication, treating or prophylaxis of AIDS, delaying the onset of AIDS, or delaying or slowing progression of AIDS), the compounds of Formula I, optionally in the form of a salt, can be administered by means that results in contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences,* 18th edition, edited by A. R. Gennaro, Mack Publishing Co., 1990 and in *Remington—The Science and Practice of Pharmacy,* 22nd Edition, published by Pharmaceutical Press and Philadelphia College of Pharmacy at University of the Sciences, 2012, ISBN 978 0 85711-062-6 and prior editions.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1 to 500 milligrams of a compound of the invention, particularly 1, 5, 10, 15, 20, 25, 50, 75, 100, 150, 200, 250, 300, 400, and 500 milligrams for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. Compounds of the invention can be administered as a single dose, once-daily or less frequently.

Unless expressly stated to the contrary, references in the preceding paragraph or elsewhere herein to the administration of a quantity of a compound of the invention are references to the quantity (i.e., amount) of the corresponding salt-free compound of Formula I.

As noted above, the present invention is also directed to use of a compound of Formula I with one or more anti-HIV agents. An "anti-HIV agent" is any agent which is directly or indirectly effective in the inhibition of HIV reverse transcriptase or another enzyme or protein required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, anti-infectives, or vaccines useful for treating HIV infection or AIDS. Suitable HIV antivirals for use in combination with the compounds of the present invention include, for example, those listed in Table 1 as follows:

TABLE 1

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | InI |
| doravirine, MK-1439 | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| Elvitegravir | InI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125, Intelence ® | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| Rilpivirine | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |
| vicriviroc | EI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, delavirdine mesylate, indinavir sulfate, atazanavir sulfate, nelfinavir mesylate, saquinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57th edition (2003), the 58th edition (2004), or the 59th edition (2005) and the current Physicians' Desk Reference (68th ed.). (2014), Montvale, N.J.: PDR Network. The dosage ranges for a compound of the invention in these combinations can be the same as those set forth above.

While not wishing to be bound by any particular theory, it is believed that the compounds of the present invention act as pro-drugs, wherein the compound is relatively stable at low pH (e.g., pH=1 to 3) but will convert by hydrolysis or cyclization to its free base at physiological pH (e.g., a pH of about 7), thereby releasing the active substance in vivo. It is believed that the phosphate group of $R^4$ is cleaved primarily in the intestines by phosphatase enzymes in the lumen and secondarily at the brush border by phosphatases releasing the active substance in vivo. The conversion can be depicted as follows:

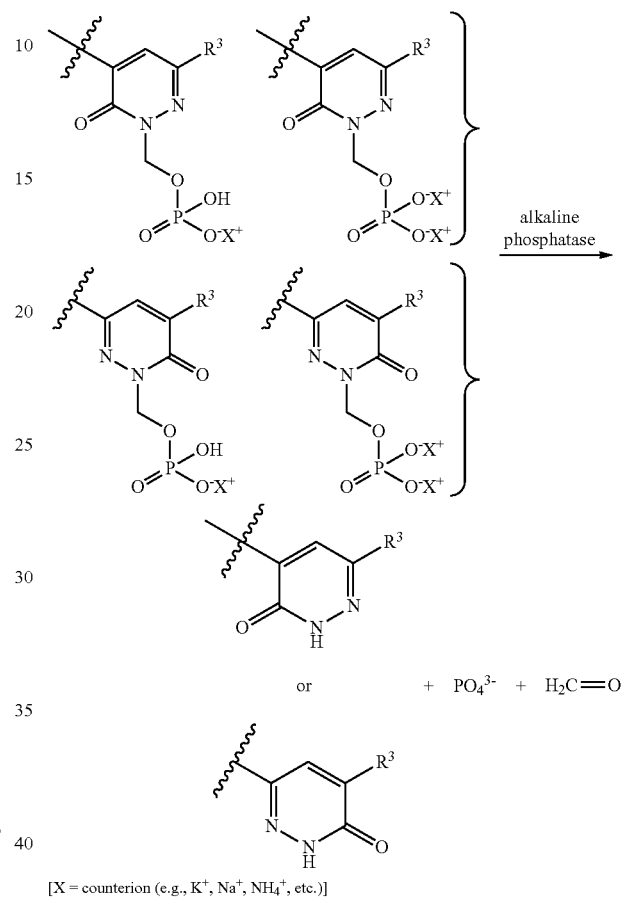

[X = counterion (e.g., $K^+$, $Na^+$, $NH_4^+$, etc.)]

Abbreviations and acronyms employed herein include the following:

AcOH = acetic acid
ACN = acetonitrile
AIDS = acquired immunodeficiency syndrome
ARC = AIDS related complex;
BSA = bovine serum albumin
CAN = ceric amonium nitrate
DAST = (diethylamino)sulfur trifluoride
DCE = 1,2-dichloroethane
DCM = dichloromethane
DEAD = diethyl azodicarboxylate
Dess-Martin periodinane = 1,1,1-Triacetoxy-1,1-dihydro-1,2-benziodoxol-3(1H)-one
DHP = 3,4-dihydro-2H-pyran
DIPEA—diisopropylethylamine
dppf = 1,1'-Bis(diphenylphosphino)ferrocene
DMF = N,N-dimethylformamide
DMSO = dimethyl sulfoxide
DNA = Deoxyribonucleic acid
EDTA = ethylenediaminetetraacetic acid
EGTA = ethylene glycol tetracetic acid
Et = ethyl
EtOAc = ethyl acetate
EtOH = ethanol -continued FBS = fetal bovine serum
HIV = human immunodeficiency virus
HPLC = high performance liquid chromatography
hr = hour
LCAP = liquid chromatography area percent
LC-MS = liquid chromatography-mass spectroscopy
LiHMDS = lithium bis(trimethylsilyl)amide
m-CPBA = 3-chloroperbenzoic acid
Me = methyl
MeOH = methanol
Me-THF = 2-methyltetrahydrofuran
mHz = megahertz
min = minute
mL = milliliters
mmol = millimoles
Ms = $SO_2CH_3$
MS (ESI) = mass spectroscopy (electrospray ionization)
NBS = N-bromosuccinimide
NHS = normal human serum
nM = nanomolar
NMP = N-methyl-2-pyrrolidinone
NMR = nuclear magnetic resonance
PBS = phosphate buffered saline
PEG = polyethylene glycol
PMB = 4-methoxybenzyl
PMBCl = 4-methoxybenzyl chloride
PPTS = 4-toluenesulfonic acid
RNA = ribonucleic acid
r.t. = room temperature
TBAF = tetrabutylammonium fluoride
TBDPS = tert-Butyldiphenylsilyl
TBS = tert-Butyldimethylsilyl
TBS-Cl = tert-Butyldimethylsilyl chloride
THP = tetrahydropyran
t-Bu = tert-butyl
t-BuOH = tert-butanol
TEA = triethylamine
TGA = thermogravimetric analysis
THF = tetrahydrofuran
TFA = trifluoroacetic acid
TFAA = trifluoroacetic anhydride
TLC = thin layer chromatography
TMSCl = trimethylsilyl chloride The following examples serve only to illustrate the invention and its practice. The examples are not to be construed as limitations on the scope or spirit of the invention. In these examples, the term "room temperature" refers to a temperature in a range of from about 20° C. to about 25° C.

Intermediate A

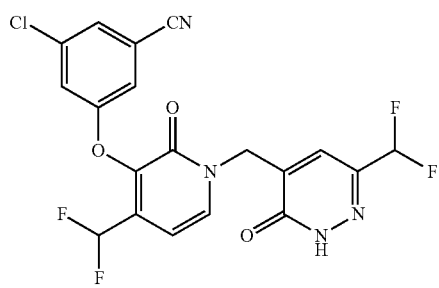

3-chloro-5-((4-(1,1-difluoroethyl)-1-((6-(difluoroethyl)-3-oxo-2,3-dihydropyridazin-4-yl)methyl)-6-oxo-1,6-dihydropyrimidin-5-yl)oxy)benzonitrile Step 1: 6-(difluoromethyl)pyrimidin-4(3H)-one

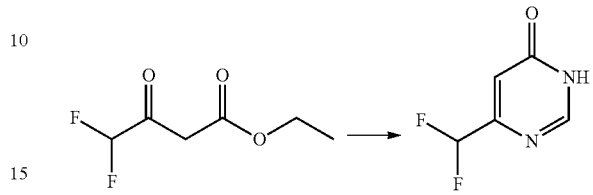

A mixture of sodium (2.91 g, 126.5 mmol) in methanol (70 mL) was stirred at r.t. for 30 minutes then formamidine acetate (6.3 g, 60 mmol) and ethyl 4,4-difluoro-3-oxobutanoate (5.0 g, 30.1 mmol) were added. The mixture was stirred at 80° C. for 4 hr. After cooling to ambient temperature, the mixture was acidified with HCl to pH=6 and extracted with ethyl acetate (200 mL×5). The combined organic layers were dried over sodium sulfate, filtered and concentrated under reduced pressure to give 6-(difluoromethyl)pyrimidin-4(3H)-one. MS (ESI): m/z 147 (M+H)+

Step 2: 6-(difluoromethyl)pyrimidin-4(3H)-one

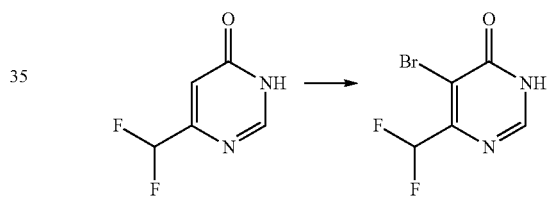

To a mixture of compound 6-(difluoromethyl)pyrimidin-4(3H)-one (2.0 g, 13.7 mmol) and potassium acetate (4.0 g, 41.4 mmol) in acetic acid (20 mL), bromine (3.3 g, 20.5 mmol) was added under nitrogen atmosphere. The resulting mixture was stirred at 80° C. for 4 hr. Then the mixture was poured into ice water and the precipitate was collected by filtration to give 5-bromo-6-(difluoromethyl)pyrimidin-4(3H)-one. MS (ESI): m/z 225, 227 (M+H)+

Step 3: 5-bromo-6-(difluoromethyl)-3-(4-methoxybenzyl)pyrimidin-4(3H)-one

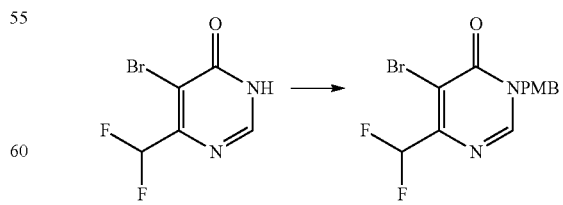

A mixture of 5-bromo-6-(difluoromethyl)pyrimidin-4 (3H)-one (1.01 g, 4.49 mmol), PMBCl (735 mg, 4.71 mmol), potassium carbonate (1.24 g, 8.98 mmol) in DMF (10 mL) was stirred at ambient temperature for 4 hr under nitrogen atmosphere. 15 mL of water was added and the precipitate was collected by filtration to give 5-bromo-6-(difluoromethyl)-3-(4-methoxybenzyl) pyrimidin-4(3H)-one. MS (ESI): m/z 345, 347 (M+H)+

Step 4: 3-chloro-5-((4-(difluoromethyl)-1-(4-methoxybenzyl)-6-oxo-1,6-dihydropyrimidin-5-yl) oxy)benzonitrile

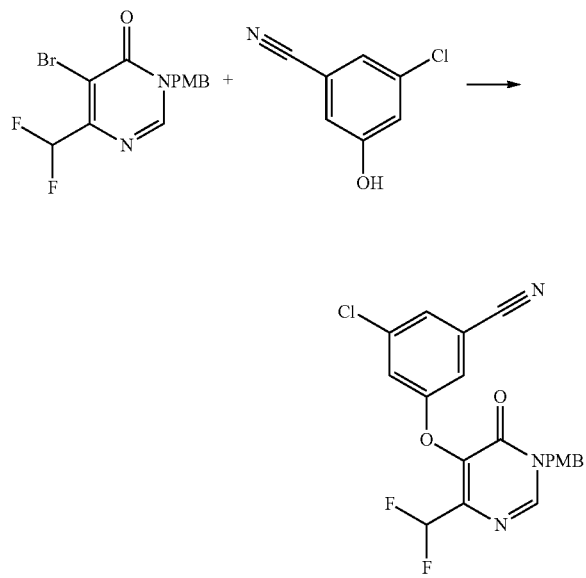

A mixture of 3-chloro-5-hydroxybenzonitrile (1.57 g, 11.6 mmol), 5-bromo-6-(difluoromethyl)-3-(4-methoxybenzyl)pyrimidin-4(3H)-one (2.0 g, 5.81 mmol) and t-BuOK (1.43 g, 12.8 mmol) in NMP (10 mL) was stirred at 120° C. overnight. After cooling to ambient temperature, the mixture was diluted with 20 mL of water and extracted with ethyl acetate (100 mL×3). The combined organic layers were dried over sodium sulfate, filtered and concentrated under reduced pressure. Then methanol (10 mL) was added and the precipitate was collected by filtration to afford 3-chloro-5-((4-(difluoromethyl)-1-(4-methoxybenzyl)-6-oxo-1,6-dihydropyrimidin-5-yl)oxy)benzonitrile. MS (ESI): m/z 418, 420 (M+H)+

Step 5: 3-chloro-5-((4-(difluoromethyl)-6-oxo-1,6-dihydropyrimidin-5-yl)oxy)benzonitrile

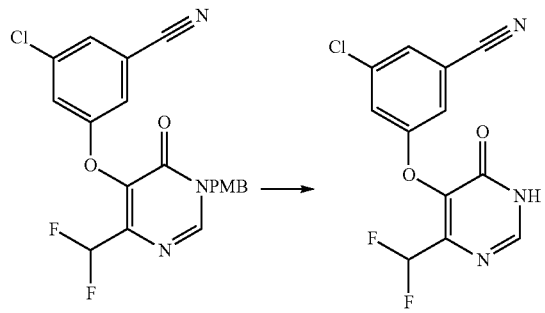

A solution of compound 3-chloro-5-((4-(difluoromethyl)-1-(4-methoxybenzyl)-6-oxo-1,6-dihydropyrimidin-5-yl) oxy)benzonitrile (400 mg, 0.96 mmol) in TFA (5 mL) was stirred under microwave irradiation at 100° C. for 10 min. After cooling to ambient temperature, the mixture was concentrated under reduced pressure. Then methanol (10 mL) was added and the precipitate was collected by filtration to provide 3-chloro-5-((4-(difluoromethyl)-6-oxo-1,6-dihydropyrimidin-5-yl)oxy) benzonitrile. MS (ESI): m/z 298, 300 (M+H)+

Step 6: 6-methoxypyridazine-3-carbaldehyde

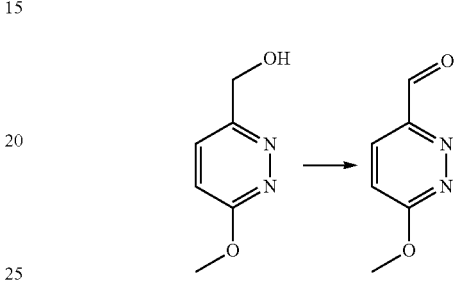

To a stirred solution of (6-methoxypyridazin-3-yl)methanol (13 g, 93 mmol) in 500 mL of anhydrous dichloromethane was added Dess-Martin periodinane (59 g, 139 mmol). The mixture was stirred for 1 hr at room temperature. The mixture was diluted with dichloromethane, washed with brine, dried over sodium sulfate, filtered and concentrated under reduced pressure. The residue was purified by chromatography on silica gel (petroleum ether:ethyl acetate (15:1 to 10:1) as eluent) to afford 6-methoxypyridazine-3-carbaldehyde. MS (ESI) m/z 139 (M+H)+

Step 7: 3-(difluoromethyl)-6-methoxypyridazine

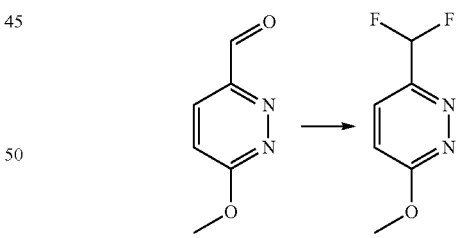

To a stirred solution of 6-methoxypyridazine-3-carbaldehyde (6.0 g, 43.4 mmol) in 100 mL of anhydrous dichloromethane was added DAST (22.7 g, 141.3 mmol). The mixture was stirred for 1 hr at room temperature. The mixture was diluted with dichloromethane, washed with aqueous sodium bicarbonate (0.5 N, 100 mL), water and brine, dried over sodium sulfate, filtered and concentrated under reduced pressure. The crude product was purified by chromatography on silica gel (petroleum ether/ethyl acetate (15:1 to 10:1) as eluent) to afford 3-(difluoromethyl)-6-methoxypyridazine. MS (ESI) m/z 161 (M+H)+

Step 8: 4-(tert-butoxymethyl)-6-(difluoromethyl)-3-methoxypyridazine

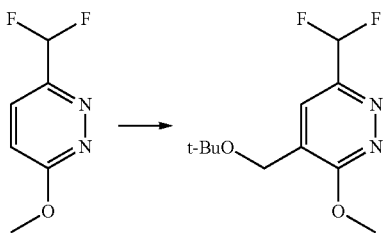 [SMILES: COc1ccc(C(F)F)nn1 ; COc1nnc(C(F)F)cc1COC(C)(C)C]

To a solution of tert-butoxy-acetic acid (0.92 g, 6.88 mmol) in THF/water (20 mol %, 7.76 mL) were added 3-(difluoromethyl)-6-methoxypyridazine (0.7 g, 4.3 mmol) and AgNO$_3$ (74 mg, 0.43 mmol). The mixture was degassed by N$_2$ with stirring at r.t. Then the mixture was heated to 70° C., and then (NH$_4$)$_2$S$_2$O$_8$ (1.7 g, 7.31 mmol) in water (10 mL) was added dropwise. After addition, the mixture was stirred at 70-80° C. for 40 mins. After cooling to r.t., the mixture was extracted with ethyl acetate (10 mL×3). The combined organic layers were washed with brine, dried over sodium sulfate, filtered and concentrated under reduced pressure. The residue was purified by chromatography on silica gel (petroleum ether/ethyl acetate (15:1 to 10:1) as eluent) to afford 4-(tert-butoxymethyl)-6-(difluoromethyl)-3-methoxypyridazine.
MS (ESI) m/z 247 (M+H)$^+$

Step 9: (6-(difluoromethyl)-3-methoxypyridazin-4-yl)methanol

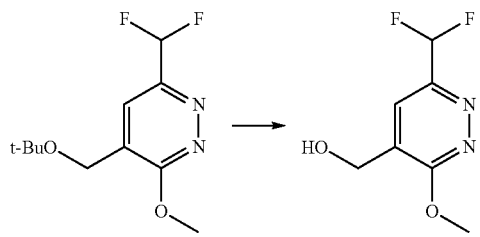 [SMILES: COc1nnc(C(F)F)cc1COC(C)(C)C ; COc1nnc(C(F)F)cc1CO]

To a solution of 4-(tert-butoxymethyl)-6-(difluoromethyl)-3-methoxypyridazine (480 mg, 1.95 mmol) in THF/DCE (1.3 mL/4.5 mL) was stirred at 60° C. for 1 hr. After cooling to r.t, the mixture was concentrated under reduced pressure. The residue was purified by preparative TLC (petroleum ether/ethyl acetate (2:1) as eluent) to give (6-(difluoromethyl)-3-methoxy pyridazin-4-yl)methanol. MS (ESI) m/z 191 (M+H)$^+$

Step 10: 4-(chloromethyl)-6-(difluoromethyl)-3-methoxypyridazine

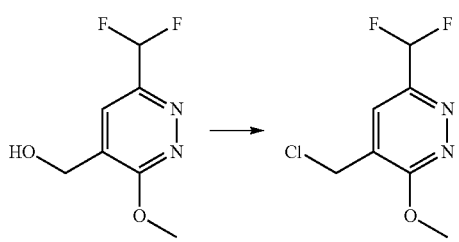

To a solution of compound (6-(difluoromethyl)-3-methoxypyridazin-4-yl)methanol (600 mg, 3.1 mmol) in anhydrous dichloromethane (20 mL) was added dropwise methansulfonyl chloride (1.08 g, 9.4 mmol) and DIPEA (1.22 g, 9.4 mmol) respectively at 0° C. The mixture was stirred at room temperature for 4 hr. Then the mixture was quenched with water and extracted with dichloromethane. The combined organic layers were dried over sodium sulfate, filtered and concentrated under reduced pressure to afford 4-(chloromethyl)-6-(difluoromethyl)-3-methoxypyridazine. MS (ESI) m/z 209, 211 (M+H)$^+$

Step 11: 3-chloro-5-((4-(difluoromethyl)-1-((6-(difluoromethyl)-3-methoxypyridazin-4-yl)methyl)-6-oxo-1,6-dihydropyrimidin-5-yl)oxy)benzonitrile

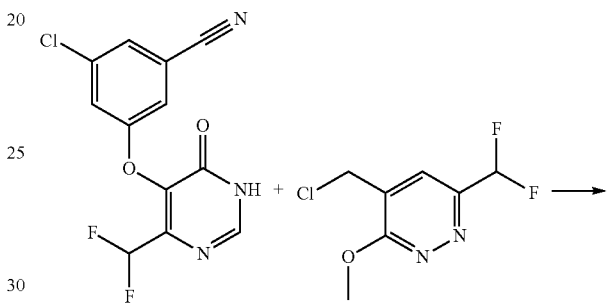

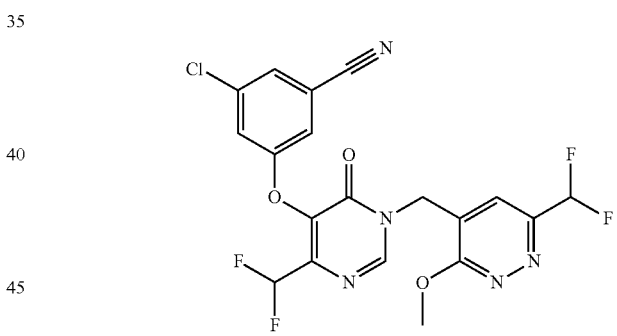

To a solution of 3-chloro-5-((4-(difluoromethyl)-6-oxo-1,6-dihydropyrimidin-5-yl)oxy)benzonitrile (150 mg, 0.5 mmol) in DMF (15 mL) were added K$_2$CO$_3$ (139 mg, 1.0 mmol), LiBr (88 mg, 1.0 mmol) and 4-(chloromethyl)-6-(difluoromethyl)-3-methoxypyridazine (105 mg, 0.5 mmol). The resulting mixture was stirred at room temperature overnight, diluted with water and extracted with EtOAc. The combined organic layers were dried over Na$_2$SO$_4$, filtered, concentrated under reduced pressure to afford 3-chloro-5-((4-(difluoromethyl)-1-((6-(difluoromethyl)-3-methoxypyridazin-4-yl)methyl)-6-oxo-1,6-dihydropyrimidin-5-yl)oxy)benzonitrile without further purification. MS (ESI) m/z 470, 472 (M+H)$^+$ Step 12: 3-chloro-5-((4-(1,1-difluoroethyl)-1-((6-(difluoroethyl)-3-oxo-2,3-dihydropyridazin-4-yl)methyl)-6-oxo-1,6-dihydropyrimidin-5-yl)oxy)benzonitrile

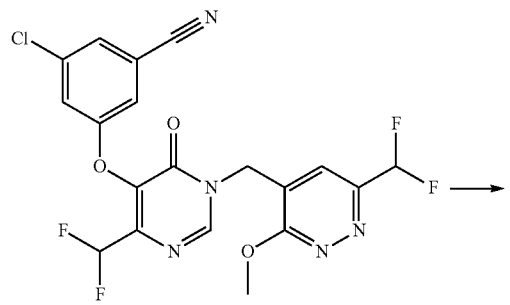

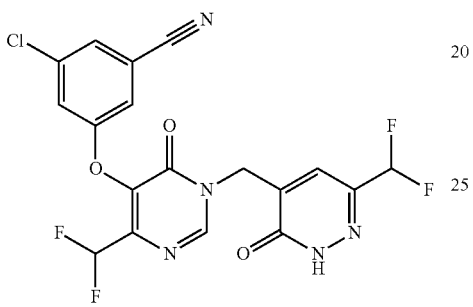

To a mixture of compound 3-chloro-5-((4-(difluoromethyl)-1-((6-(difluoromethyl)-3-methoxypyridazin-4-yl)methyl)-6-oxo-1,6-dihydropyrimidin-5-yl)oxy)benzonitrile (200 mg, 0.42 mmol) and KI (142 mg, 0.84 mmol) in acetonitrile (3 mL) was added TMSCl (93 mg, 0.84 mmol) at room temperature. The resulting mixture was stirred at 70° C. for 1.5 hr. After cooled to r.t., the mixture was diluted with EtOAc and washed with aq. $Na_2S_2O_3$ and brine, dried over anhydrous $Na_2SO_4$ and concentrated under reduced pressure. The residue was purified by preparative HPLC to afford the desired product 3-chloro-5-((4-(difluoromethyl)-1-((6-(difluoromethyl)-3-oxo-2,3-dihydropyridazin-4-yl)methyl)-6-oxo-1,6-dihydropyrimidin-5-yl)oxy)benzonitrile. $^1$H NMR: (Methanol-$d_4$, 400 MHz) δ 13.60 (s, 1H), 8.66 (s, 1H), 7.71 (s, 1H), 7.62 (s, 2H), 7.59 (s, 1H), 6.98 (t, J=52.0 Hz, 1H), 6.77 (t, J=54.0 Hz, 1H), 4.97 (s, 2H).
MS (ESI) m/z 456, 458 (M+H)$^+$ Example 1

(5-((5-(3-chloro-5-cyanophenoxy)-4-(difluoromethyl)-6-oxopyrimidin-1(6H)-yl)methyl)-3-(difluoromethyl)-6-oxopyridazin-1(6H)-yl)methyl dihydrogen phosphate

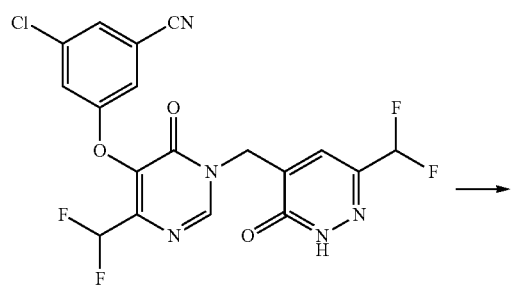

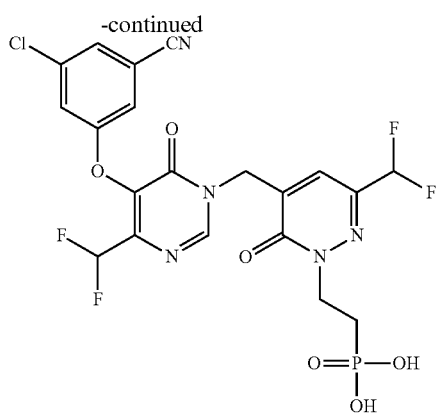

The above compound was prepared by following similar procedures as described in Example 7 steps 1-2. $^1$H NMR (500 MHz, DMSO-d6) δ 8.70 (s, 1H), 7.65-7.75 (m, 4H), 6.74-7.02 (m, 2H), 5.71 (d, J=7.8 Hz, 2H), 5.06 (s, 2H). MS: 566 (M+H)$^+$ Intermediate B

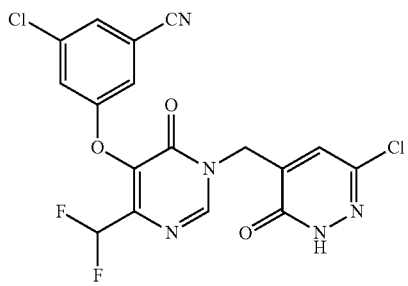 [SMILES: N#Cc1cc(Cl)cc(Oc2c(C(F)F)ncn(Cc3cc(Cl)n[nH]c3=O)c2=O)c1]

3-chloro-5-((1-((6-chloro-3-oxo-2,3-dihydropyridazin-4-yl)methyl)-4-(difluoromethyl)-6-oxo-1,6-dihydropyrimidin-5-yl)oxy)benzonitrile Step 1: Methyl 3,6-dichloropyridazine-4-carboxylate

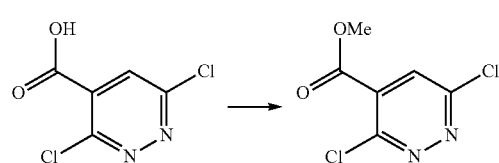 [SMILES: O=C(O)c1cc(Cl)nnc1Cl ; COC(=O)c1cc(Cl)nnc1Cl]

A suspension of 3,6-dichloropyridazine-4-carboxylic acid (5.5 g, 28.5 mmol) in DCM (50.0 ml) and MeOH (10 ml) was added trimethylsilyldiazomethane (2 M in hexane, 15 ml, 30.0 mmol) slowly at 0° C. It became a clear solution after the addition. It was stirred for 30 min and was added another 15 mL of trimethylsilyldiazomethane and stirred for 30 min. It was quenched with 2 mL of acetic acid, concentrated and purified by ISCO (80 g, 0-40% ethyl acetate in hexane) to give the title compound. MS (ESI): m/z 206 (M+H)$^+$

Step 2: Methyl 6-chloro-3-methoxypyridazine-4-carboxylate

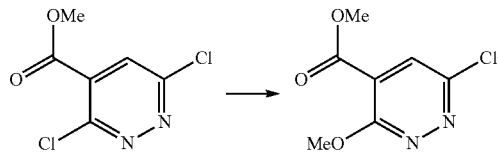 [SMILES: COC(=O)c1cc(Cl)nnc1Cl ; COC(=O)c1cc(Cl)nnc1OC]

Methyl 3,6-dichloropyridazine-4-carboxylate (2 g, 9.66 mmol) was weighted into a clean dry flask charged with a magnetic stirring bar. It was sealed and purged with nitrogen twice and dissolved in anhydrous THF (40 ml). The solution was cooled in an ice-water bath and added sodium methoxide (0.69 g, 12.77 mmol) in one portion. It was stirred for 30 min. LC-MS showed the completion of the reaction. It was quenched with saturated aqueous ammonium chloride (20 mL). The mixture was extracted with ethyl acetate (3×40 mL). The combined organic layers were washed with brine, dried over sodium sulfate, filtered and concentrated. The residue was purified by ISCO (80 g, 0-30% ethyl acetate in hexane) to give the title compound. MS (ESI): m/z 203 (M+H)$^+$

Step 3: 6-Chloro-3-methoxypyridazine-4-carboxylic acid

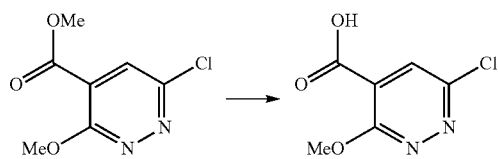 [SMILES: COC(=O)c1cc(Cl)nnc1OC ; COc1nnc(Cl)cc1C(=O)O]

A solution of methyl 6-chloro-3-methoxypyridazine-4-carboxylate (510 mg, 2.52 mmol) in tetrahydrofuran (5 ml) and methanol (5.00 mL) was treated with 4 M aqueous LiOH (5 mL, 20.00 mmol) for 15 min. It was neutralized by 1 N HCl and concentrated. The residue was dried under vacuum and used without purification. MS (ESI): m/z 189 (M+H)$^+$

Step 4: (6-Chloro-3-methoxypyridazin-4-yl)methanol

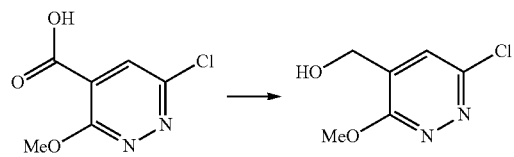 [SMILES: COc1nnc(Cl)cc1C(=O)O ; COc1nnc(Cl)cc1CO]

A mixture of 6-chloro-3-methoxypyridazine-4-carboxylic acid (270 mg, 1.432 mmol) and carbonyldiimidazole (697 mg, 4.30 mmol) in THF (12 mL) was stirred for 1 h at rt. The solution was cooled to 0° C. and added sodium borohydride (271 mg, 7.16 mmol) followed by water (4 ml). It was stirred for 15 min and quenched with 5 mL of saturated aqueous ammonium chloride, extracted with ethyl acetate (4×20 mL). The combined organic layers were washed with brine (5 mL), dried over sodium sulfate, filtered and concentrated. The residue was purified by ISCO (40 g, 0-50% ethyl acetate in hexane) to give the title compound. MS (ESI): m/z 175 (M+H)$^+$

Step 5: 6-Chloro-4-(chloromethyl)-3-methoxypyridazine

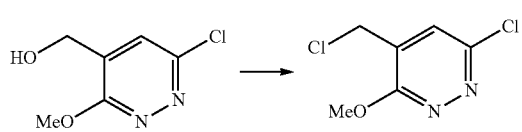 [SMILES: COc1nnc(Cl)cc1CO ; COc1nnc(Cl)cc1CCl]

To a solution of (6-chloro-3-methoxypyridazin-4-yl)methanol (100 mg, 0.573 mmol) in DCM (5 ml) at 0° C. was added methanesulfonyl chloride (0.134 ml, 1.718 mmol) and Hunig's Base (0.300 ml, 1.718 mmol). It was stirred at 0° C. for 15 min and allowed to warm to rt overnight. It was concentrated under reduced pressure. The residue was purified by ISCO (24 g, 0-30% EtOAc/Hexanes gradient) to afford the title compound. MS (ESI): m/z 192 (M+H)$^+$

Step 6: 3-chloro-5-((1-((6-chloro-3-methoxypyridazin-4-yl)methyl)-4-(difluoromethyl)-6-oxo-1, 6-dihydropyrimidin-5-yl)oxy)benzonitrile

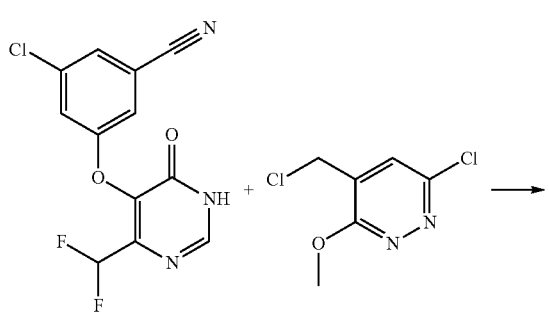

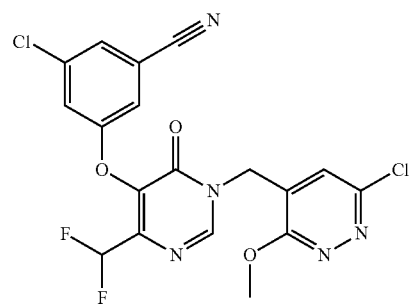

Compound was prepared in the same as manner as Intermediate A, step 11.

Step 7: 3-chloro-5-(1-((6-chloro-3-oxo-2,3-dihydro-pyridazin-4-yl)methyl)-4-(difluoromethyl)-6-oxo-1,6-dihydropyrimidin-5-yl)oxy)benzonitrile

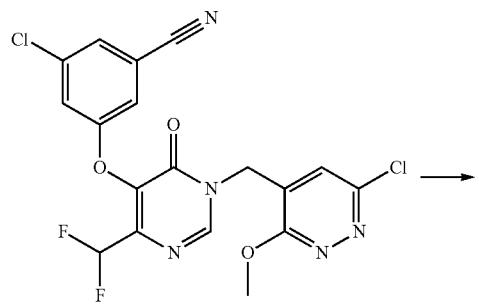

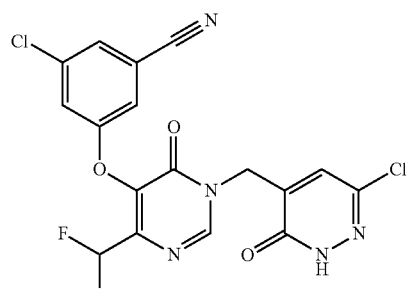

Compound was prepared in the same as manner as Intermediate A, step 12.

$^1$H NMR: (DMSO-d$_6$, 500 MHz) δ 8.66 (s, 1H), 7.75 (s, 1H), 7.69 (s, 1H), 7.65 (m, 1H), 7.54 (s, 1H), 7.02 (t, J=52.0 Hz, 1H), 4.96 (s, 2H). MS (ESI) m/z 440.1 (M+H)$^+$

Example 2

(3-chloro-5-((5-(3-chloro-5-cyanophenoxy)-4-(difluoromethyl)-6-oxopyrimidin-1(6H)-yl)methyl)-6-oxopyridazin-1(6H)-yl)methyl dihydrogen phosphate

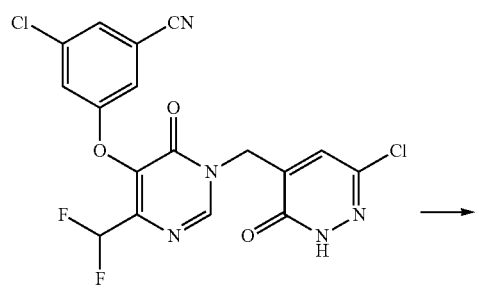

-continued

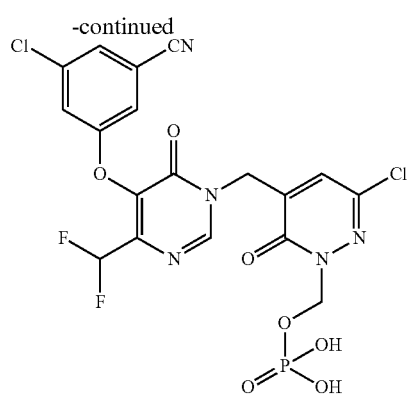

The above compound was prepared by following similar procedures as described in Example 7 steps 1-2. $^1$H NMR (500 MHz, DMSO-d6) δ 8.66 (s, 1H), 7.64-7.75 (m, 4H), 7.03 (t, J=55 Hz, 1H), 5.63 (d, J=8.05 Hz, 2H), 5.01 (s, 2H). MS: 550 (M+H)$^+$ Intermediate C

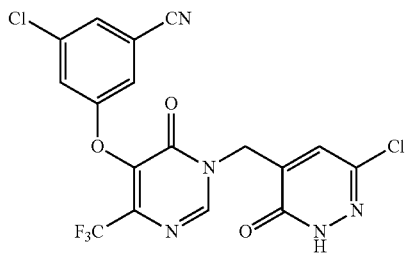 [SMILES: N#Cc1cc(Cl)cc(Oc2c(C(F)(F)F)ncn(Cc3cc(Cl)n[nH]c3=O)c2=O)c1]

3-chloro-5-((1-((6-chloro-3-oxo-2,3-dihydro-pyridazin-4-yl)methyl)-6-oxo-4-(trifluoromethyl)-1,6-dihydropyrimidin-5-yl)oxy)benzonitrile Step 1

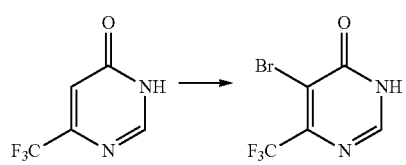 [SMILES: O=c1cc(C(F)(F)F)nc[nH]1 ; O=c1[nH]cnc(C(F)(F)F)c1Br]

*Eur. J. Org. Chem.* 2004, 3714-37188.

Step 2:
5-bromo-6-(trifluoromethyl)-4(3H)-pyrimidione

To a solution of 6-(trifluoromethyl)pyrimidin-4(3H)-one (0.3 g, 1.8 mmol) in acetic acid (2 mL) was added CH$_3$COOK (0.54 g, 5.5 mmol). Then to the mixture was added a solution of Br$_2$ in acetic acid (1 mL) dropwise. The mixture was heated to 80° C. and stirred overnight. After cooling to room temperature, the mixture was diluted with EtOAc, washed with water and brine, dried over Na$_2$SO$_4$, and evaporated to afford 5-bromo-6-(trifluoromethyl)-4 (3H)-pyrimidione.

Step 3: 5-bromo-3-(4-methoxybenzyl)-6-(trifluoromethyl)pyrimidin-4(3H)-one

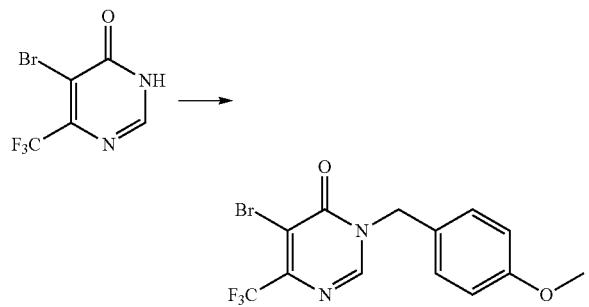

To a solution of 5-bromo-6-(trifluoromethyl)pyrimidin-4 (3H)-one (190 mg, 0.91 mmol) in DMF (2 mL) was added K$_2$CO$_3$ (250 mg, 1.82 mmol) and PMBCl (210 mg, 1.3 mmol). The mixture was stirred at room temperature for 5 hr. The mixture was poured into water, and extracted with EtOAc (40 mL×3). The organic layer was washed with water and brine, dried over anhydrous Na$_2$SO$_4$ and concentrated. The residue was purified by column chromatography on silica gel (petroleum ether/ethyl acetate (5:1 to 1:1) as eluent) to afford 1 5-bromo-3-(4-methoxybenzyl)-6-(trifluoromethyl)pyrimidin-4(3H)-one. $^1$H-NMR J000159069 H11896-016-3 CDCl$_3$, 400 MHz δ 7.97 (s, 1H, ArH), 7.27 (d, J=8.8, 2H, ArH), 6.87 (d, J=8.8, 2H, ArH), 5.04 (s, 2H, CH), 3.78 (s, 3H, CH).

Step 4: 3-chloro-5-(1-(4-methoxybenzyl)-6-oxo-4-(trifluoromethyl)-1,6-dihydropyrimidin-5-yloxy) benzonitrile

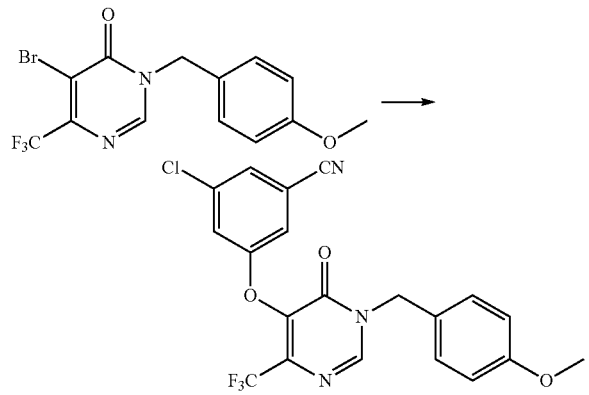

To a solution of 5-bromo-3-(4-methoxybenzyl)-6-(trifluoromethyl)pyrimidin-4(3H)-one (5 g, 13.8 mmol) in NMP (50 mL) was added K$_2$CO$_3$ (5.7 g, 41.3 mmol) and 3-chloro-5-hydroxybenzonitrile (3.2 g, 20.7 mmol). The mixture was stirred at 120° C. for 20 hr. The mixture was poured into water, and extracted with EtOAc (60 mL×3). The organic layer was washed with water and brine, dried over anhydrous Na$_2$SO$_4$, and concentrated. The residue was purified by column chromatography (petroleum ether/ethyl acetate (5:1 to 1:1) as eluent) to afford 3-chloro-5-(1-(4-methoxybenzyl)-6-oxo-4-(trifluoromethyl)-1,6-dihydropyrimidin-5-yloxy)benzonitrile.

$^1$H-NMR J000169946 H11896-128-3 DMSO, 400 MHz δ 8.86 (s, 1H, ArH), 7.76 (s, 1H, ArH), 7.70 (s, 1H, ArH), 7.68 (s, 1H, ArH), 7.34 (d, J=8.6, 2H, ArH), 6.90 (d, J=8.6, 2H, ArH), 5.10 (s, 2H, CH), 3.72 (s, 3H, CH).

Step 5: 3-chloro-5-(6-oxo-4-(trifluoromethyl)-1,6-dihydropyrimidin-5-yloxy)benzonitrile

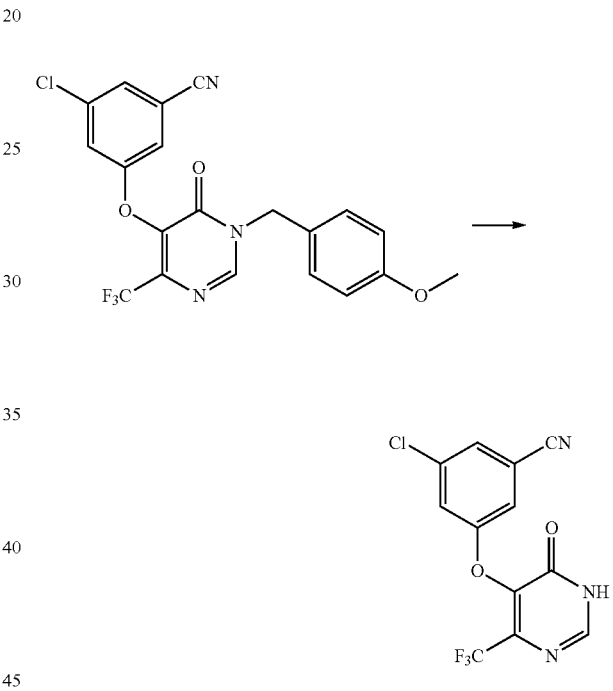

To a solution of 3-chloro-5-(1-(4-methoxybenzyl)-6-oxo-4-(trifluoromethyl)-1,6-dihydropyrimidin-5-yloxy)benzonitrile (2 g, 4.6 mmol) in CH$_3$CN (20 mL) and H$_2$O (8 mL) was added C$_e$(NH$_4$)$_2$(NO$_3$)$_6$ (10 g, 18.4 mmol) in portions. The mixture was stirred at room temperature overnight and then poured into water, and extracted with EtOAc (60 mL×3). The organic layer was washed with water and brine, dried over anhydrous Na$_2$SO$_4$, and concentrated. The residue was purified by column chromatography on silica gel (petroleum ether/ethyl acetate (5:1 to 1:1) as eluent) to afford 3-chloro-5-(6-oxo-4-(trifluoro methyl)-1,6-dihydropyrimidin-5-yloxy)benzonitrile. $^1$H-NMR J000170654 H11896-138-3 DMSO, 400 MHz δ 13.59 (s, 1H, NH), 8.36 (s, 1H, ArH), 7.76 (s, 1H, ArH), 7.73 (s, 1H, ArH), 7.70 (s, 1H, ArH).

Step 6: 3-chloro-5-((1-((6-chloro-3-methoxy-pyridazin-4-yl)methyl)-6-oxo-4-(trifluoromethyl)-1,6-dihydropyrimidin-5-yl)oxy)benzonitrile

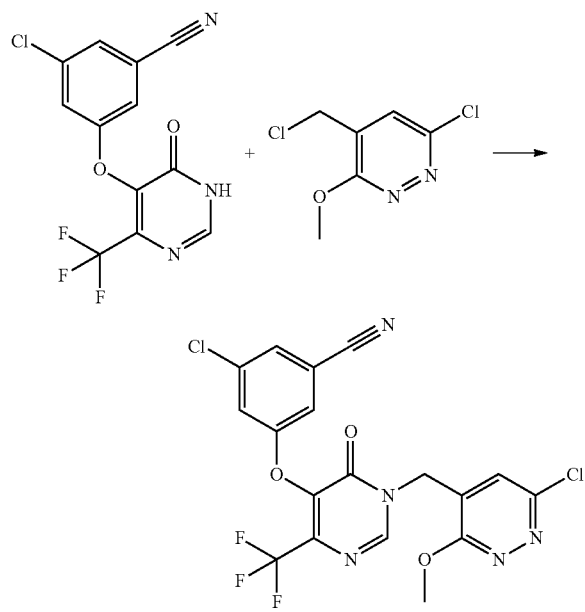

To a solution of 3-chloro-5-((6-oxo-4-(trifluoromethyl)-1,6-dihydropyrimidin-5-yl)oxy)benzonitrile (100 mg, 0.32 mmol) in DMF (5 mL) were added 6-chloro-4-(chloromethyl)-3-methoxypyridazine (55 mg, 0.29 mmol, Example 2, step 5) and $K_2CO_3$ (80 mg, 0.58 mmol). The resulting mixture was stirred was stirred at 80° C. for 2 hours. After cooling to room temperature, the mixture was diluted with water and extracted with EtOAc. The combined organic layers were dried over sodium sulfate, filtered and concentrated under reduced pressure to give the desired product 3-chloro-5-((1-(((6-chloro-3-methoxy-2,3-dihydropyridazin-4-yl)methyl)-6-oxo-4-(trifluoromethyl)-1,6-dihydropyrimidin-5-yl)oxy)benzonitrile, which was used for the next step without further purification. MS (ESI) m/z 472, 474, 476 (M+H)$^+$ Step 7: 3-chloro-5-((1-(((6-chloro-3-oxo-2,3-dihydropyridazin-4-yl)methyl)-6-oxo-4-(trifluoromethyl)-1,6-dihydropyrimidin-5-yl)oxy)benzonitrile

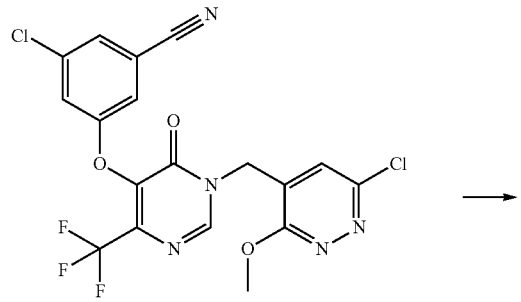

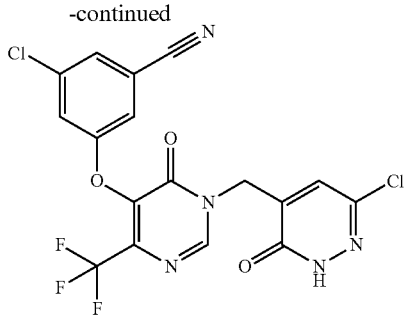

To a mixture of compound 3-chloro-5-((1-(((6-chloro-3-methoxypyridazin-4-yl)methyl)-6-oxo-4-(trifluoromethyl)-1,6-dihydropyrimidin-5-yl)oxy)benzonitrile (110 mg, 0.23 mmol) and KI (77 mg, 0.46 mmol) in acetonitrile (10 mL) was added TMSCl (50 mg, 0.46 mmol) at room temperature. The resulting mixture was stirred for 1 hour at 70° C. After cooling to r.t., the mixture was diluted with EtOAc and washed with aq. $Na_2S_2O_3$ and brine, dried over anhydrous $Na_2SO_4$ and concentrated in vacuum. The residue was purified by Prep-HPLC to afford 3-chloro-5-((1-(((6-chloro-3-oxo-2,3-dihydropyridazin-4-yl)methyl)-6-oxo-4-(trifluoromethyl)-1,6-dihydropyrimidin-5-yl)oxy)benzonitrile. $^1$H NMR (Methanol-$d_4$, 400 MHz): δ 8.60 (s, 1H), 7.68 (s, 1H), 7.47 (s, 1H), 7.28 (s, 1H), 7.24 (s, 1H), 5.07 (s, 2H), 1.92 (t, J=18.4 Hz, 6H). MS (ESI) m/z 458, 460, 462 (M+H)$^+$ Example 3

(3-chloro-5-((5-(3-chloro-5-cyanophenoxy)-6-oxo-4-(trifluoromethyl)pyrimidin-1(6H)-yl)methyl)-6-oxopyridazin-1(6H)methyl dihydrogen phosphate

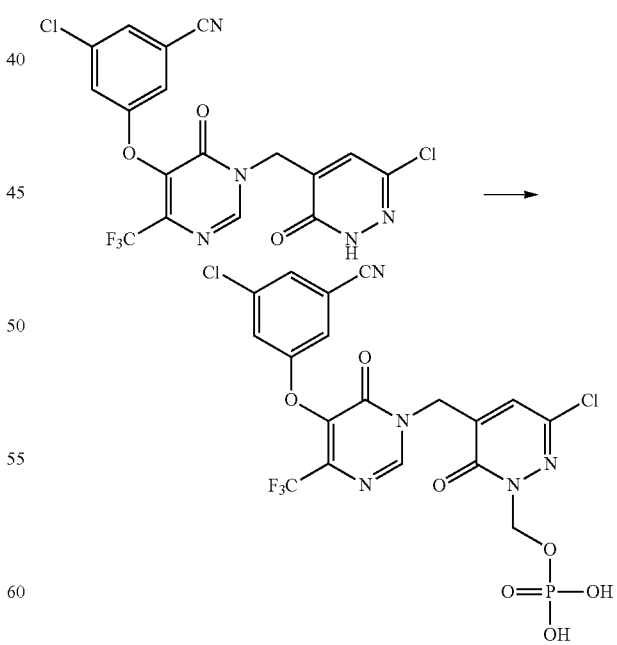

The above compound was prepared by following similar procedures as described in Example 7 steps 1-2. $^1$H NMR (500 MHz, DMSO-d6) 8.79 (s, 1H), 7.80-7.70 (m, 3H), 7.70 (s, 1H), 5.60 (d, 2H), 5.00 (s, 2H). MS: 568 (M+H)$^+$

Intermediate D

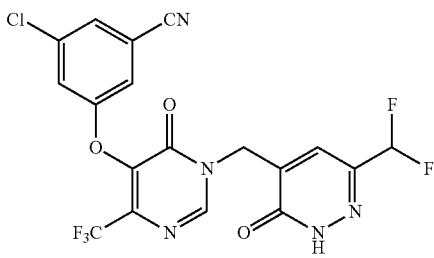 [SMILES: N#Cc1cc(Cl)cc(Oc2c(C(F)(F)F)ncn(Cc3cc(C(F)F)n[nH]c3=O)c2=O)c1]

3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile Step 1: methyl 5-(hydroxymethyl)-6-methoxypyridazine-3-carboxylate

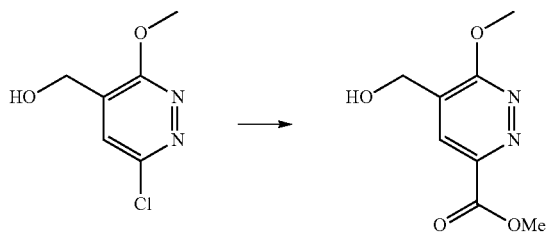

To a solution of (6-chloro-3-methoxypyridazin-4-yl)methanol (4.6 g, 26.4 mmol), triethyl amine (7.4 mL) and Pd(dppf)$_2$Cl$_2$ (0.5 g, 1 mmol) in 30 mL of methanol and ethyl acetate (10 mL) was stirred under carbon monoxide (50 psi) at 70° C. overnight. Then the reaction mixture was poured into water, extracted with ethyl acetate (15 mL×3). The organic extracts were washed with water and brine, dried over anhydrous sodium sulfate, filtered and concentrated under reduced pressure. The residue was purified by column (petroleum ether/ethyl acetate (5:1 to 2:1) as eluent) to give methyl 5-(hydroxymethyl)-6-methoxypyridazine-3-carboxylate. MS (ESI) m/z 199 (M+H)$^+$ Step 2: methyl 5-(((tert-butyldimethylsilyl)oxy)methyl)-6-methoxypyridazine-3-carboxylate

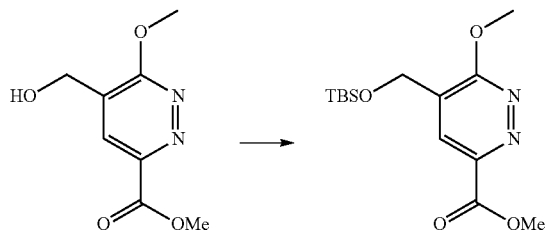 [SMILES: COC(=O)c1cc(CO)c(OC)nn1 ; COC(=O)c1cc(CO[Si](C)(C)C(C)(C)C)c(OC)nn1]

To a solution of methyl 5-(hydroxymethyl)-6-methoxypyridazine-3-carboxylate (2.1 g, 10.6 mmol) in THF (150 mL) was added TBSCl (4.55 g, 30.2 mmol) and imidazole (2.05 g, 30.2 mmol) at r.t. Then the resulting reaction was stirred at room temperature overnight. The reaction mixture was filtered and the filtrate was washed with water. The organic layer was dried over magnesium sulfate, filtered and concentrated under reduced pressure to afford methyl 5-(((tert-butyldimethylsilyl)oxy)methyl)-6-methoxypyridazine-3-carboxylate. MS (ESI) m/z 313 (M+H)$^+$ Step 3: (5-(((tert-butyldimethylsilyl)oxy)methyl)-6-methoxypyridazin-3-yl)methanol

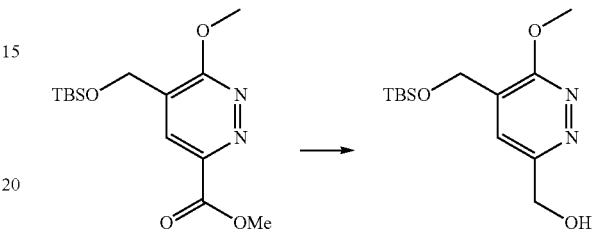

To a solution of methyl 5-(((tert-butyldimethylsilyl)oxy)methyl)-6-methoxypyridazine-3-carboxylate (2.1 g, 6.7 mmol) in ethanol (15 mL) was added NaBH$_4$ (0.38 g, 10.0 mmol) and CaCl$_2$ (0.37 g, 3.4 mmol) at 0° C. The mixture was stirred for 1 hr at room temperature, then quenched by addition of water (20 mL), acidified to pH=8 using HCl solution (2 M) and extracted with ethyl acetate (15 mL×3). The combined organic extracts were dried over sodium sulfate, filtered and concentrated under reduced pressure to give (5-(((tert-butyldimethylsilyl) oxy)methyl)-6-methoxypyridazin-3-yl)methanol. MS (ESI) m/z 285 (M+H)$^+$ Step 4: 4-(((tert-butyldimethylsilyl)oxy)methyl)-3-methoxy-6-(((tetrahydro-2H-pyran-2-yl)oxy)methyl)pyridazine

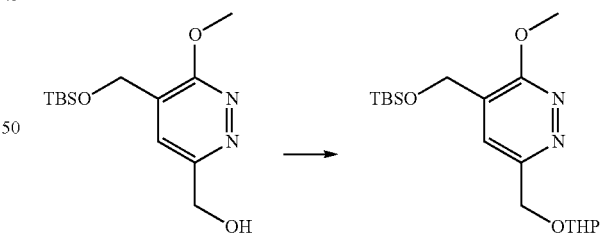

To a solution of (5-(((tert-butyldimethylsilyl)oxy)methyl)-6-methoxypyridazin-3-yl)methanol (1.5 g, 5.3 mmol) in acetonitrile (10 mL) was added DHP (0.53 g, 6.3 mmol) and PPTS (126 mg, 0.5 mmol) at r.t. The mixture was stirred at 80° C. for 16 hr. After cooling to r.t., the mixture was concentrated under reduced pressure. The residue was purified by column chromatography on a silica gel (petroleum ether/ethyl acetate (10:1) as eluent) to give 4-(((tert-butyldimethylsilyl)oxy)methyl)-3-methoxy-6-(((tetrahydro-2H-pyran-2-yl)oxy)methyl)pyridazine. MS (ESI) m/z 369 (M+H)$^+$

Step 5: (3-methoxy-6-(((tetrahydro-2H-pyran-2-yl)oxy)methyl)pyridazin-4-yl)methanol

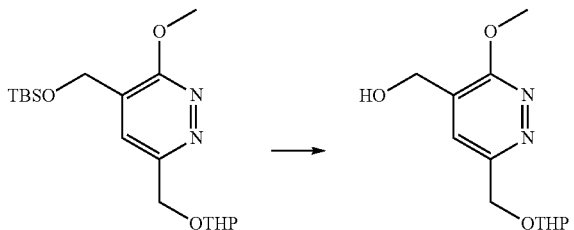

A solution of 4-(((tert-butyldimethylsilyl)oxy)methyl)-3-methoxy-6-(((tetrahydro-2H-pyran-2-yl)oxy)methyl)pyridazine (0.9 g, 2.4 mmol) and TBAF (3.2 g, 12.2 mmol) in THF (20.0 mL) was stirred for 1.0 h at r.t. Water was added and the resulting mixture was extracted with ethyl acetate. The combined organics were dried over sodium sulfate, filtered and concentrated under reduced pressure. The residue was purified by preparative TLC (petroleum ether/ethyl acetate (1:2) as eluent) to give the (3-methoxy-6-(((tetrahydro-2H-pyran-2-yl)oxy)methyl)pyridazin-4-yl)methanol. MS (ESI) m/z 255 (M+H)$^+$

Step 6: 3-chloro-5-(0-((3-methoxy-6-(((tetrahydro-2H-pyran-2-yl)oxy)methyl)pyridazin-4-yl)methyl)-6-oxo-4-(trifluoromethyl)-1,6-dihydropyrimidin-5-yl)oxy)benzonitrile

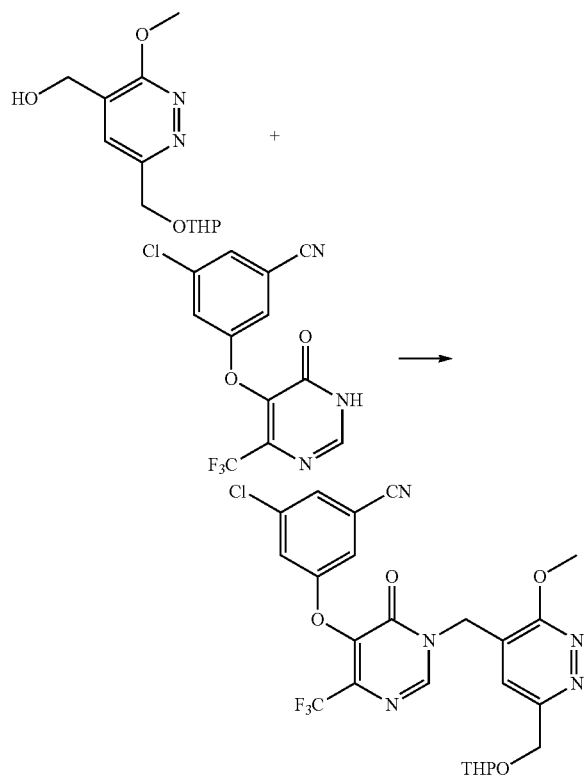

To a solution of (3-methoxy-6-(((tetrahydro-2H-pyran-2-yl)oxy)methyl) pyridazin-4-yl)methanol (0.6 g, 2.4 mmol), 3-chloro-5-((6-oxo-4-(trifluoromethyl)-1,6-dihydropyrimidin-5-yl)oxy)benzonitrile (0.76 g, 2.4 mmol, Example 3, step 5) and triphenylphosphine (1.3 g, 4.8 mmol) in dichloromethane (10.0 mL) was added DEAD (0.84 g, 4.8 mmol) at 0° C. under a nitrogen atmosphere. The mixture was stirred at r.t for 1 h, quenched with water (10 mL) and extracted with dichloromethane (20 mL×3). The combined organic extracts were dried over sodium sulfate, filtered and concentrated under reduced pressure. The crude product was purified by preparative TLC (petroleum ether/ethyl acetate (1:1) as eluent) to give 3-chloro-5-((1-((3-methoxy-6-(((tetrahydro-2H-pyran-2-yl)oxy)methyl)pyridazin-4-yl)methyl)-6-oxo-4-(trifluoromethyl)-1,6-dihydropyrimidin-5-yl)oxy)benzonitrile. MS (ESI) m/z 552, 554 (M+H)$^+$

Step 7: 3-chloro-5-((1-((6-(hydroxymethyl)-3-methoxypyridazin-4-yl)methyl)-6-oxo-4-(trifluoromethyl)-1,6-dihydropyrimidin-5-yl)oxy)benzonitrile

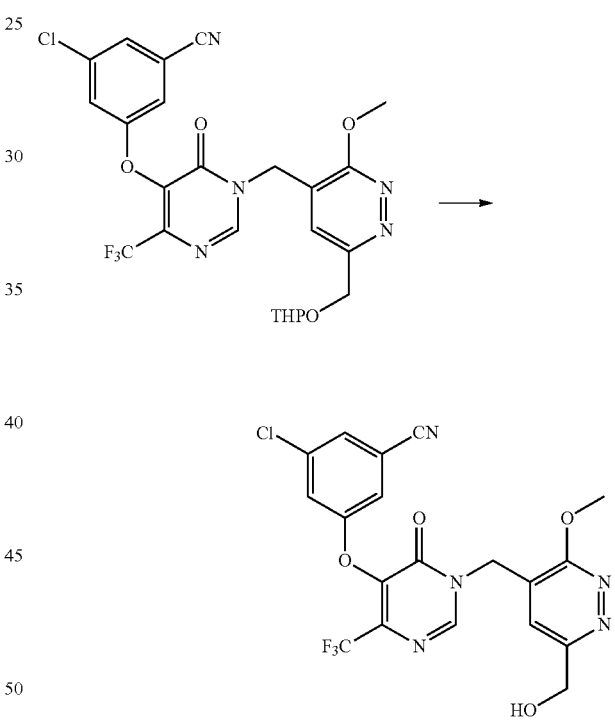

To a solution of 3-chloro-5-((1-((3-methoxy-6-(((tetrahydro-2H-pyran-2-yl)oxy)methyl) pyridazin-4-yl)methyl)-6-oxo-4-(trifluoromethyl)-1,6-dihydropyrimidin-5-yl)oxy) benzonitrile (1.2 g, 2.2 mmol) in methanol (10 mL) was added HCl/methanol (1 N, 10 mL) at r.t. The resulting mixture was stirred at room temperature for 1 hr and concentrated under reduced pressure to give 3-chloro-5-((1-((6-(hydroxymethyl)-3-methoxypyridazin-4-yl)methyl)-6-oxo-4-(trifluoromethyl)-1,6-dihydropyrimidin-5-yl)oxy) benzonitrile. MS (ESI) m/z 468, 470 (M+H)$^+$

Step 8: 3-chloro-5-((1-((6-formyl-3-methoxy-pyridazin-4-yl)methyl)-6-oxo-4-(trifluoromethyl)-1,6-dihydropyrimidin-5-yl)oxy)benzonitrile

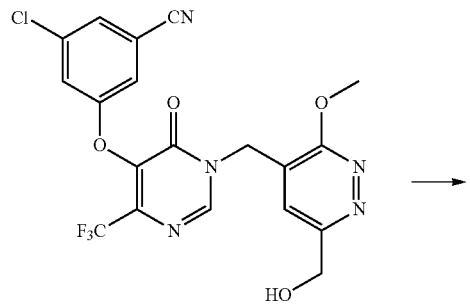

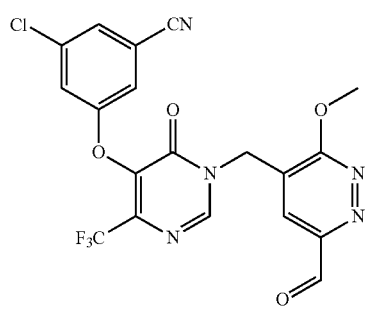

To a solution of 3-chloro-5-((1-((6-(hydroxymethyl)-3-methoxypyridazin-4-yl) methyl)-6-oxo-4-(trifluoromethyl)-1,6-dihydropyrimidin-5-yl)oxy)benzonitrile (1.0 g, 2.1 mmol) in dichloromethane (20 mL) was added Dess-Martin periodinane (1.36 g, 3.2 mmol) at 0° C. under a nitrogen atmosphere. The mixture was stirred at r.t for 1 hr, quenched with water (10 mL) and extracted with dichloromethane (20 mL×3). The combined organic extracts were dried over sodium sulfate, filtered and concentrated under reduced pressure. The crude product was purified by preparative TLC (petroleum ether/ethyl acetate (1:1) as eluent) to give 3-chloro-5-((1-((6-formyl-3-methoxypyridazin-4-yl) methyl)-6-oxo-4-(trifluoromethyl)-1,6-dihydropyrimidin-5-yl)oxy) benzonitrile. MS (ESI) m/z 466, 468 (M+H)$^+$

Step 9: 3-chloro-5-((1-((6-(difluoromethyl)-3-methoxypyridazin-4-yl)methyl)-6-oxo-4-(trifluoromethyl)-1,6-dihydropyrimidin-5-yl)oxy)benzonitrile

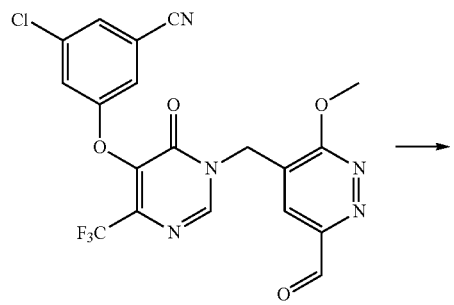

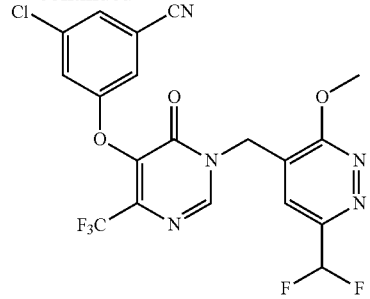

To a stirred mixture of 3-chloro-5-((1-((6-formyl-3-methoxypyridazin-4-yl)methyl)-6-oxo-4-(trifluoromethyl)-1,6-dihydropyrimidin-5-yl)oxy)benzonitrile (0.14 g, 0.3 mmol) in dichloromethane (5 mL) was added DAST (0.43 g, 1.6 mmol) at r.t., and the mixture was stirred under a nitrogen atmosphere for 16 hr. The mixture was quenched with H$_2$O and extracted with dichloromethane. The organic layer was washed with water, dried over anhydrous sodium sulfate, filtered and concentrated under reduced pressure. The residue was purified by chromatography on silica gel (petroleum ether/ethyl acetate (2:1) as eluent) to give 3-chloro-5-((1-((6-(difluoromethyl)-3-methoxypyridazin-4-yl)methyl)-6-oxo-4-(trifluoromethyl)-1,6-dihydropyrimidin-5-yl)oxy)benzonitrile. MS (ESI) m/z 488, 490 (M+H)$^+$

Step 10: 3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile

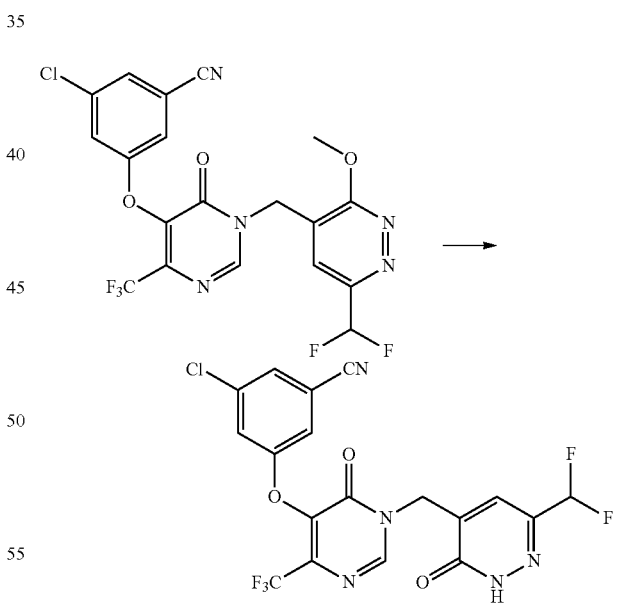

To a mixture of 3-chloro-5-((1-((6-(difluoromethyl)-3-methoxypyridazin-4-yl) methyl)-6-oxo-4-(trifluoromethyl)-1,6-dihydropyrimidin-5-yl)oxy)benzonitrile (90 mg, 0.2 mmol) and KI (100 mg, 0.6 mmol) in acetonitrile (3 mL) was added TMSCl (33 mg, 0.3 mmol). The mixture was stirred at r.t for 1 hr, quenched with water and extracted with ethyl acetate. The combined organic extracts were washed with brine, dried over sodium sulfate, filtered and concentrated under reduced pressure. The residue was purified by preparative HPLC to afford 3-chloro-5-((1-((6-(difluoromethyl)-3-oxo-2,3-dihydropyridazin-4-yl)methyl)-6-oxo-4-(trifluoromethyl)-1,6-dihydropyrimidin-5-yl)oxy)benzonitrile. ¹HNMR (Methanol-d4, 400 MHz) δ 13.62 (s, 1H), 8.72 (s, 1H), 7.73 (s, 1H), 7.71 (s, 1H), 7.68 (s, 1H), 7.66 (s, 1H), 6.78 (t, J=56.0 Hz, 1H), 4.99 (s, 2H). MS (ESI) m/z 474, 476 (M+H)⁺

Example 4

(5-((5-(3-chloro-5-cyanophenoxy)-6-oxo-4-(trifluoromethyl)pyrimidin-1(6H)-yl)methyl)-3-(difluoromethyl)-6-oxopyridazin-1(6H)-yl)methyl dihydrogen phosphate

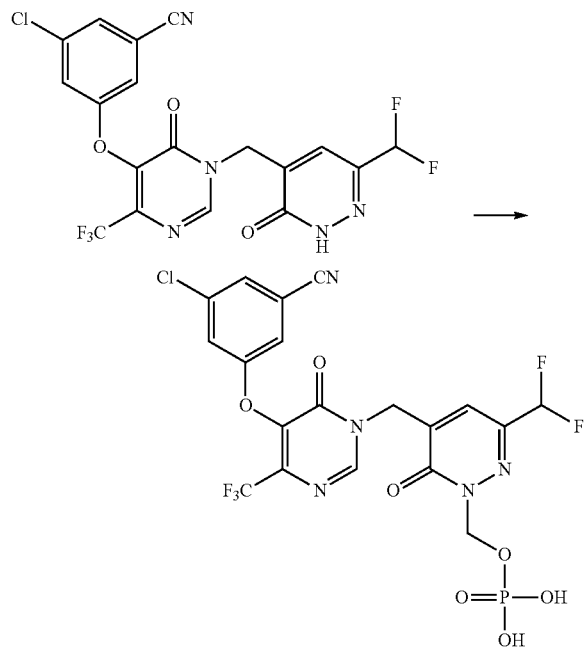

The above compound was prepared by following similar procedures as described in Example 7 steps 1-2. ¹H NMR (500 MHz, DMSO-d6) δ 8.76 (s, 1H), 7.72-7.78 (m, 4H), 6.85 (t, J=53 Hz, 1H), 5.71 (d, J=7.81 Hz, 2H), 5.08 (s, 2H). MS: 584 (M+H)⁺

Intermediate E

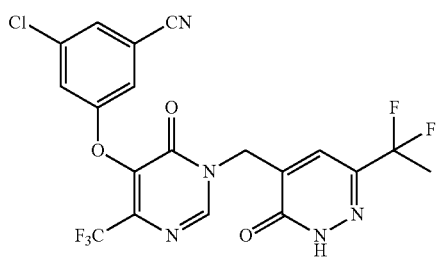 [SMILES: CC(F)(F)c1cc(Cn2cnc(C(F)(F)F)c(Oc3cc(Cl)cc(C#N)c3)c2=O)c(=O)[nH]n1]

3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile Step 1: 4-(tert-butoxymethyl)-6-(1-ethoxyvinyl)-3-methoxypyridazine

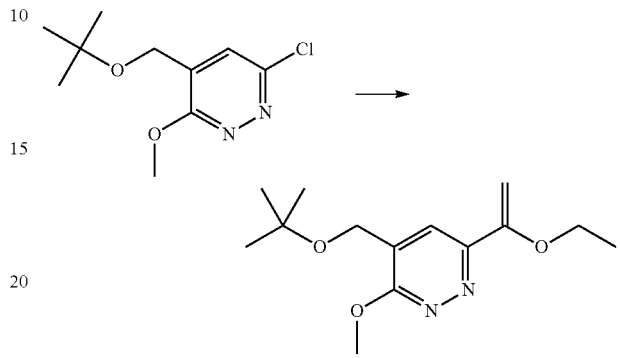

To a mixture of 4-(tert-butoxymethyl)-6-chloro-3-methoxypyridazine (1 g, 5.7 mmol), tributyl(1-ethoxyvinyl)stannane (6.2 g, 17.2 mmol) in toluene (10 mL) was added Pd(PPh₃)₄ (0.6 g, 0.57 mmol) under N₂. The resulting suspension was stirred at 120° C. overnight under a nitrogen atmosphere. After cooling to r.t., the mixture was poured into ice-water, extracted with ethyl acetate, and the combined organic extracts were washed with brine, dried over sodium sulfate, filtered and concentrated under reduced pressure. The residue was purified by column chromatography on silica gel (petroleum ether/ethyl acetate (5:1 to 2:1) as eluent) to afford 4-(tert-butoxymethyl)-6-(1-ethoxyvinyl)-3-methoxypyridazine. MS (ESI): m/z 267 (M+H)⁺

Step 2: 1-(5-(tert-butoxymethyl)-6-methoxypyridazin-3-yl)ethanone

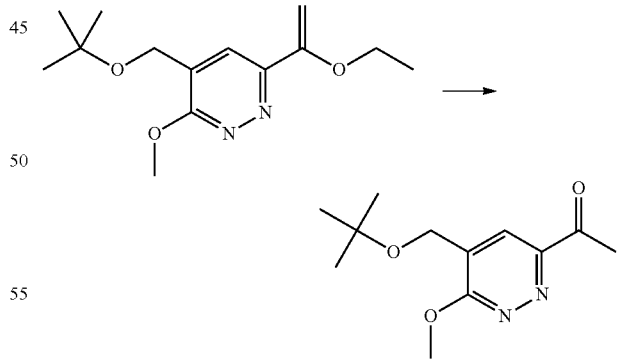

To a solution of 4-(tert-butoxymethyl)-6-(1-ethoxyvinyl)-3-methoxypyridazine (400 mg, 1.5 mmol) in 1,4-dioxane (6 mL) was added HCl/1,4-dioxane (3N, 6 mL), the solution was stirred at room temperature overnight. The mixture was diluted with water and extracted with ethyl acetate. The combined organic extracts were dried over anhydrous sodium sulfate, filtered and concentrated under reduced pressure. The residue was purified by prepreative TLC (petroleum ether/ethyl acetate (1:1) as eluent) to give 1-(5-(tert-butoxymethyl)-6-methoxy pyridazin-3-yl) ethanone. MS (ESI) m/z 239 (M+H)⁺

Step 3: 4-(tert-butoxymethyl)-6-(1,1-difluoroethyl)-3-methoxypyridazine

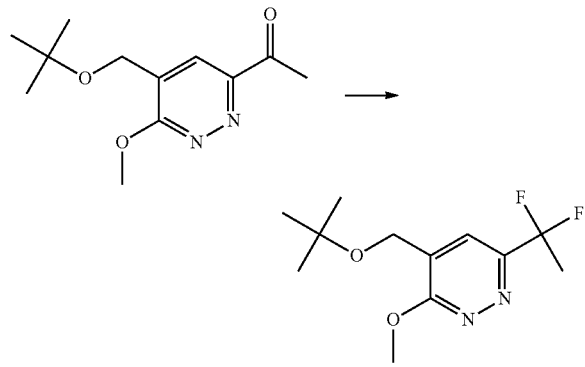

To a solution of 1-(5-(tert-butoxymethyl)-6-methoxypyridazin-3-yl)ethanone (240 mg, 1.0 mmol) in dichloromethane (8 mL) was added DAST (0.8 mL, 6.1 mmol). The mixture was stirred at r.t. for 4 hr. LCMS showed that the reaction was completed. The mixture was quenched with water and extracted with ethyl acetate. The combined organic extracts were dried over anhydrous sodium sulfate, filtered and concentrated under reduced pressure to give 4-(tert-butoxymethyl)-6-(1,1-difluoroethyl)-3-methoxypyridazine. MS (ESI) m/z 261 (M+H)⁺

Step 4: (6-(1,1-difluoroethyl)-3-methoxypyridazin-4-yl)methanol

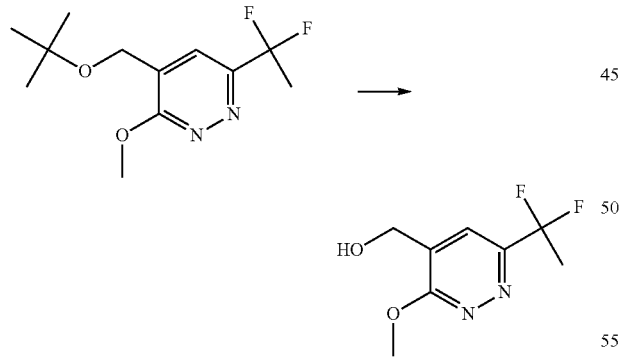

To a solution of 4-(tert-butoxymethyl)-6-(1,1-difluoroethyl)-3-methoxypyridazine (150 mg, 0.58 mmol) in dichloromethane (8 mL) was added 4N HO/methanol (3 mL). The mixture was stirred at room temperature for 3 hr, then quenched with water and extracted with dichloromethane. The organic layer was dried over anhydrous sodium sulfate, concentrated under reduced pressure and purified by preparative TLC (petroleum ether/ethyl acetate (1:1.5) as eluent) to give (6-(1,1-difluoroethyl)-3-methoxypyridazin-4-yl)methanol. MS (ESI) m/z 205 (M+H)⁺

Step 5: (6-(1,1-difluoroethyl)-3-methoxypyridazin-4-yl)methyl methanesulfonate

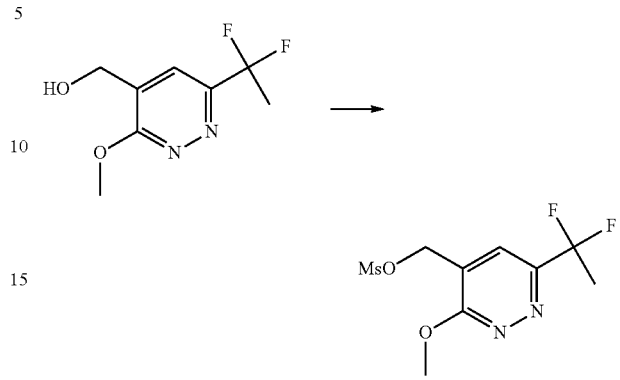

To a solution of (6-(1,1-difluoroethyl)-3-methoxypyridazin-4-yl)methanol (110 mg, 0.54 mmol) in dichloromethane (6 mL) was added DIPEA (209 mg, 1.6 mmol) and methanesulfonyl chloride (75 mg, 0.62 mmol) dropwise. The mixture was stirred at room temperature for 2 hr. The mixture was diluted with water and extracted with dichloromethane. The organic layer was dried over anhydrous sodium sulfate, filtered and concentrated under reduced pressure to give (6-(1,1-difluoroethyl)-3-methoxypyridazin-4-yl)methyl methanesulfonate. MS (ESI) m/z 283 (M+H)⁺

Step 6: 3-chloro-5-((1-(((6-(1,1-difluoroethyl)-3-methoxypyridazin-4-yl)methyl)-6-oxo-4-(trifluoromethyl)-1,6-dihydropyrimidin-5-yl)oxy)benzonitrile

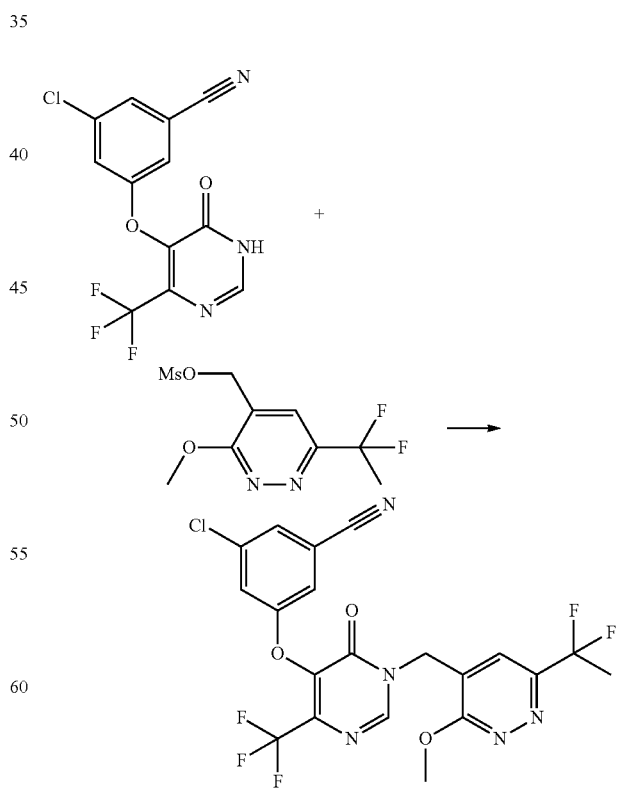

To a solution of (6-(1,1-difluoroethyl)-3-methoxypyridazin-4-yl)methyl methanesulfonate (120 mg, 0.54 mmol) in DMF (5 mL) was added 3-chloro-5-((6-oxo-4-(trifluoromethyl)-1,6-dihydropyrimidin-5-yl)oxy)benzonitrile (187 mg, 0.59 mmol, Example 3, step 5), TEA (0.23 mL, 1.6 mmol). The mixture was stirred at 30° C. for 2 hr. After cooling to r.t., the mixture was diluted with water, extracted with ethyl acetate. The organic layer was dried over anhydrous sodium sulfate, filtered and concentrated under reduced pressure to give 3-chloro-5-((1-((6-(1,1-difluoroethyl)-3-methoxypyridazin-4-yl)methyl)-6-oxo-4-(trifluoromethyl)-1,6-dihydropyrimidin-5-yl)oxy)benzonitrile. MS (ESI) m/z 502, 504 (M+H)+

Step 7: 3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile

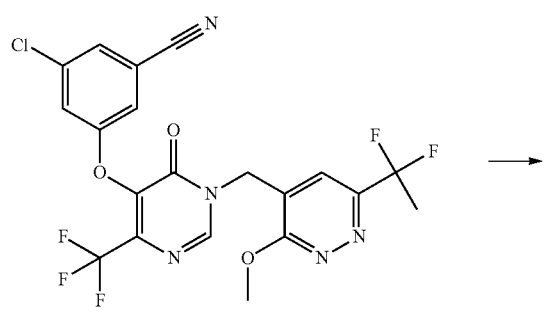

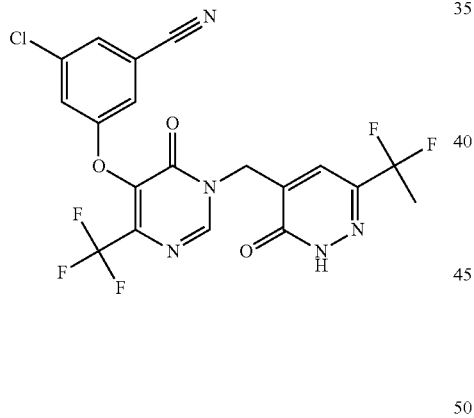

To a mixture of 3-chloro-5-((1-((6-(1,1-difluoroethyl)-3-methoxypyridazin-4-yl)methyl)-6-oxo-4-(trifluoromethyl)-1,6-dihydropyrimidin-5-yl)oxy)benzonitrile (120 mg, 0.24 mmol) and KI (79.5 mg, 0.48 mmol) in acetonitrile (4 mL) was added TMSCl (51.7 mg, 0.48 mmol) dropwise at r.t. After addition, the mixture was stirred at 30° C. for 3 hr. After cooling to r.t., the mixture was quenched with MeOH and concentrated under reduce pressure. The residue was purified by preparative HPLC to afford 3-chloro-5-((1-((6-(1,1-difluoroethyl)-3-oxo-2,3-dihydropyridazin-4-yl)methyl)-6-oxo-4-(trifluoromethyl)-1,6-dihydropyrimidin-5-yl)oxy)benzonitrile. $^1$H NMR (DMSO-d6, 400 MHz): δ 13.53 (s, 1H), 8.72 (s, 1H), 7.67-7.72 (m, 4H), 5.10 (s, 2H), 1.85-1.90 (m, 3H). MS (ESI): m/z 488, 490 (M+H)+

Example 5

(5-((5-(3-chloro-5-cyanophenoxy)-6-oxo-4-(trifluoromethyl)pyrimidin-1(6H)-yl)methyl)-3-(1,1-difluoroethyl)-6-oxopyridazin-1(6H)-yl)methyl dihydrogen phosphate

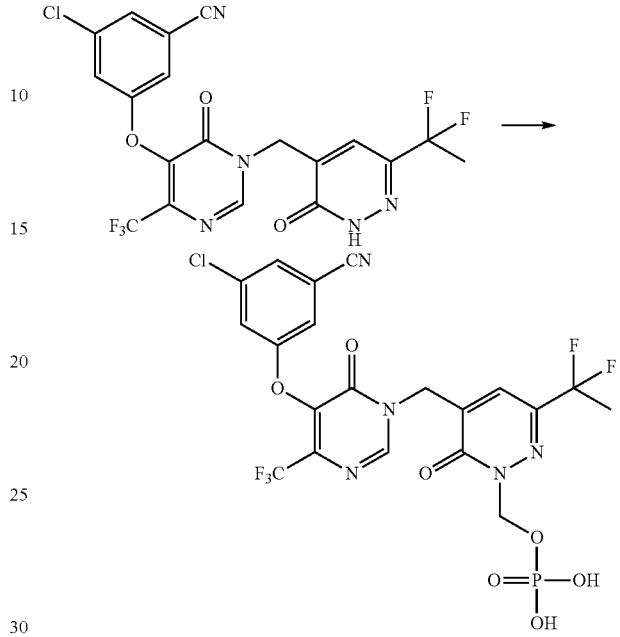

The above compound was prepared by following similar procedures as described in Example 7 steps 1-2. $^1$H NMR (500 MHz, DMSO-d6) 8.90 (s, 1H), 7.80-7.70 (m, 4H), 5.70 (d, 2H), 5.05 (s, 2H), 2.0-1.95 (t, 3H). MS: 598 (M+H)+

Intermediate F

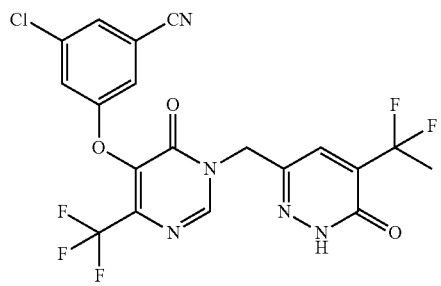 [SMILES: CC(F)(F)c1cc(Cn2cnc(C(F)(F)F)c(Oc3cc(Cl)cc(C#N)c3)c2=O)n[nH]c1=O]

3-chloro-5-((6-oxo-1-((6-oxo-5-(trifluoromethyl)-1,6-dihydropyridazin-3-yl) methyl)-4-(trifluoromethyl)-1,6-dihydropyrimidin-5-yl)oxy)benzonitrile Step 1: 6-(bromomethyl)-4-(trifluoromethyl) pyridazin-3(2H)-one

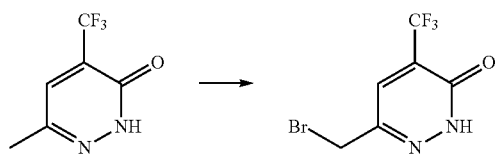

To a mixture of 6-methyl-4-(trifluoromethyl)pyridazin-3 (2H)-one (2 g, 11.2 mmol) in 20 mL of CCl₄ was added NBS (3 g, 17.2 mmol) and benzoyl peroxide (100 mg) at r.t. The resulting mixture was heated at reflux for 18 hr. LCMS showed the reaction completed, the mixture was poured into ice-water and extracted with dichloromethane. The combined extracts were dried and concentrated under reduced pressure. The residue was purified by column chromatography on silica gel (petroleum ether/ethyl acetate (5:1) as eluent) to afford 6-(bromomethyl)-4-(trifluoromethyl)pyridazin-3(2H)-one.

Step 2: 3-chloro-5-((6-oxo-1-((6-oxo-5-(trifluoromethyl)-1,6-dihydropyridazin-3-yl) methyl)-4-(trifluoromethyl)-1,6-dihydropyrimidin-5-yl)oxy)benzonitrile

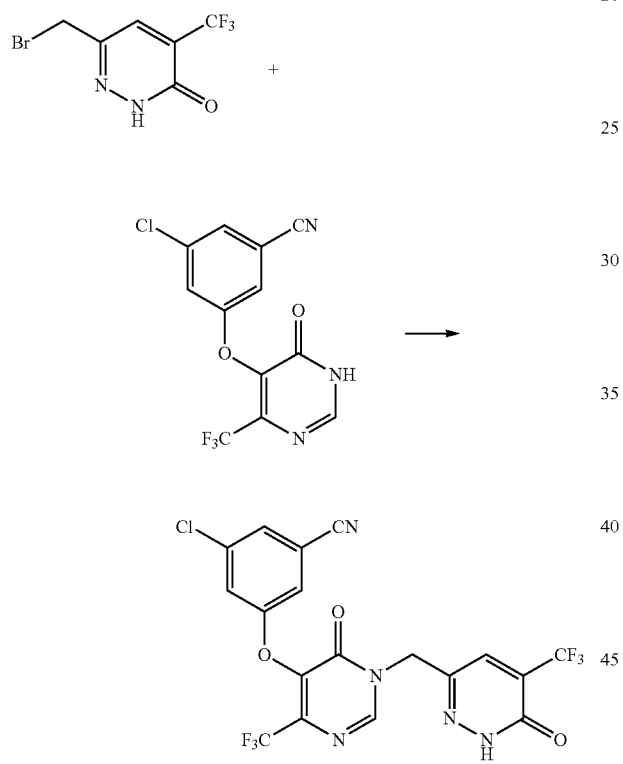

A mixture of 3-chloro-5-(6-oxo-4-(trifluoromethyl)-1,6-dihydropyrimidin-5-yloxy) benzonitrile (400 mg, 1.27 mmol, Example 3, step 5), 6-(bromomethyl)-4-(trifluoromethyl)pyridazin-3(2H)-one (260 mg, 1.0 mmol) and potassium carbonate (170 mg, 1.23 mmol) in DMF (6 mL) was stirred at room temperature for 18 hr. The mixture was diluted with water, extracted with ethyl acetate. The combined organic layers were washed with water and brine, dried over sodium sulfate, filtered and under reduced pressure. The residue was purified by preparative HPLC to afford 3-chloro-5-((6-oxo-1-((6-oxo-5-(trifluoromethyl)-1,6-dihydropyridazin-3-yl) methyl)-4-(trifluoromethyl)-1,6-dihydropyrimidin-5-yl)oxy)benzonitrile. ¹H NMR (DMSO-d6, 400 MHz): δ 13.72 (s, 1H), 8.77 (s, 1H), 8.02 (s, 1H), 7.78 (s, 1H), 7.71 (s, 1H), 7.68 (s, 1H), 5.19 (s, 2H). MS (ESI) m/z 492, 494 (M+H)⁺

Example 6

Sodium (3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl phosphate Step 1: di-tert-butyl ((3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl) phosphate

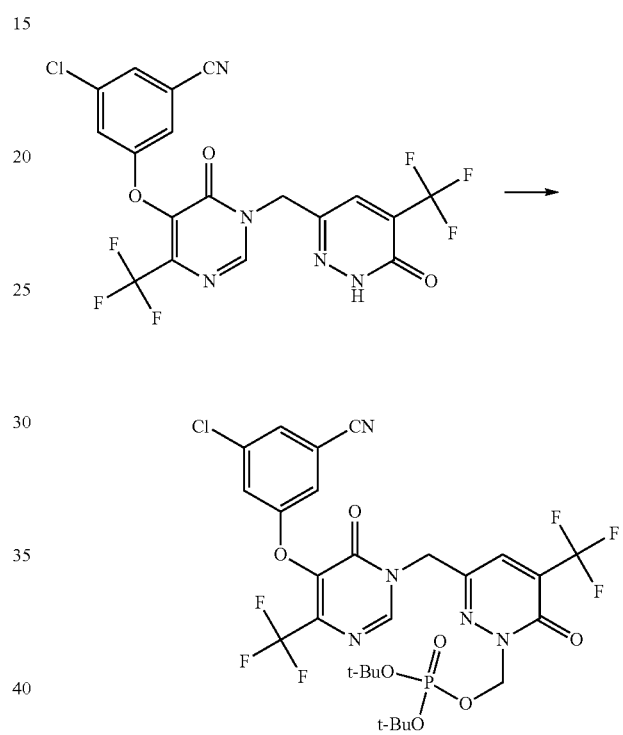

To a solution of 3-chloro-5-((6-oxo-1-((6-oxo-5-(trifluoromethyl)-1,6-dihydropyridazin-3-yl)methyl)-4-(trifluoromethyl)-1,6-dihydropyrimidin-5-yl)oxy)benzonitrile (1.5 g, 3.05 mmol) in Dioxane:DMF (5:1, 25 mL) was added potassium carbonate (0.843 g, 6.1 mol). The reaction mixture was stirred at room temperature for 0.5 h. Phosphoric acid di-tert-butyl ester chloromethyl ester (1.19 g, 4.58 mmol) was added at −30° C. The resulting mixture was stirred at 40° C. for 2.5 h under microwave. After cooled to r.t., the reaction mixture was poured into water and extracted with ethyl acetate. The combined organic layer was dried over sodium sulfate and concentrated in vacuum. The residue was purified by prep. HPLC to afford the desired product di-tert-butyl ((3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl) phosphate. MS (ESI): m/z 736 (M+Na)+. ¹H NMR (400 MHz, DMSO-d6) δ 8.75 (s, 1H), 8.13 (s, 1H), 7.63-7.74 (m, 3H), 5.59 (d, J=8.0 Hz, 2H), 5.21 (s, 2H).

Step 2: sodium (3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl phosphate

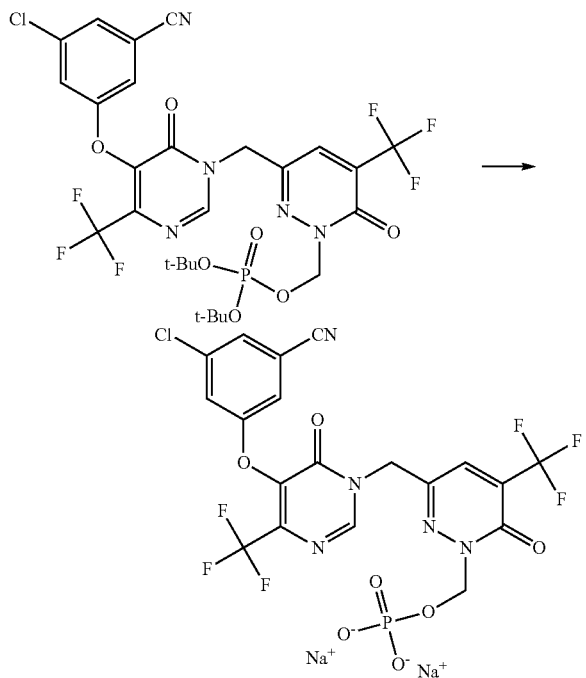

To a solution of di-tert-butyl ((3-((5-(3-chloro-5-cyano-phenoxy)-6-oxo-4-(trifluoromethyl)pyrimidin-1(6H)-yl)methyl)-6-oxo-5-(trifluoromethyl)pyridazin-1(6H)-yl)methyl) phosphate (260 mg, 0.36 mmol) in dichloromethane (7 mL) was added a solution of CF₃COOH (0.14 mL) in dichloromethane (0.5 mL). After stirred at room temperature for 2 h, the mixture was concentrated in vacuum. The residue was dissolved in methanol (5 mL), then sodium acetate (59.8 mg, 0.73 mmol) in methanol (0.6 mL) was added. The resulting mixture was stirred overnight at room temperature. The mixture was lyophilized and the solid was washed with methanol and dried in vacuum to afford sodium (3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl phosphate. ¹H NMR (DMSO&D₂O, 400 MHz) δ 8.65 (s, 1H), 7.95 (s, 1H), 7.60-7.69 (m, 3H), 5.59 (d, J=8.4 Hz, 2H), 5.14 (s, 2H).

Intermediate G

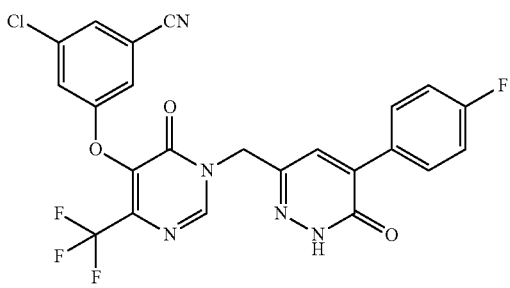 [SMILES: N#Cc1cc(Cl)cc(Oc2c(C(F)(F)F)ncn(Cc3cc(-c4ccc(F)cc4)c(=O)[nH]n3)c2=O)c1]

3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile Step 1: ethyl 2-(4-fluorophenyl)-2-oxoacetate

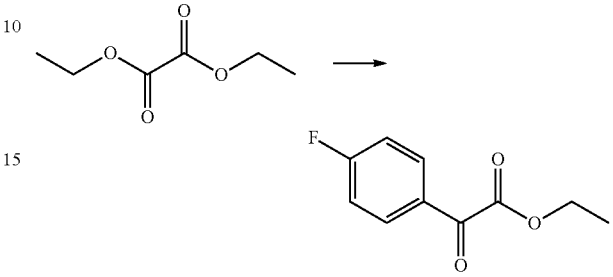

Into a 10-L round-bottom flask purged and maintained with an inert atmosphere of nitrogen, was placed a solution of diethyl oxalate (360 g, 2.46 mol, 1.00 equiv) in tetrahydrofuran (3000 mL). This was followed by the addition of a solution of 4-fluorophenylmagnesium bromide in tetrahydrofuran (1.9 L, 1 N 0.78 equiv) dropwise with stirring at −78° C. in 2.5 hr. The resulting solution was stirred for 30 min at −78° C., then slowly warmed to −20° C. The reaction was then quenched by the addition of 500 mL of 2 M HCl. The resulting solution was extracted with 2×500 mL of ethyl acetate and the organic layers combined. The resulting mixture was washed with 2×200 mL of brine. The mixture was dried over anhydrous magnesium sulfate and concentrated under reduced pressure. The crude product was purified by distillation under reduced pressure (5 mm Hg) and the fraction was collected at 106° C. to provide ethyl 2-(4-fluorophenyl)-2-oxoacetate.

Step 2: ethyl 5-((tert-butyldiphenylsilyl)oxy)-2-(4-fluorophenyl)-2-hydroxy-4-oxopentanoate

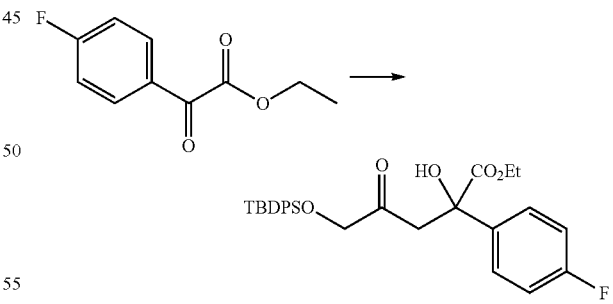

Into a 250-mL sealed tube purged and maintained with an inert atmosphere of nitrogen, was placed ethyl 2-(4-fluorophenyl)-2-oxoacetate (55 g, 280 mmol, 1.00 equiv), 1-[(tert-butyldiphenylsilyl)oxy]propan-2-one (110 g, 352 mmol, 1.26 equiv), acetic acid (33 g, 550 mmol, 1.96 equiv), pyrrolidine (7.8 g, 93 mmol, 0.33 equiv). The resulting solution was stirred overnight at 85° C. and then applied onto a silica gel column with ethyl acetate/petroleum ether (1:60-1:10) to obtain ethyl 5-[(tert-butyldiphenylsilyl)oxy]-2-(4-fluorophenyl)-2-hydroxy-4-oxopentanoate.

Step 3: 6-[[(tert-butyldiphenylsilyl)oxy]methyl]-4-(4-fluorophenyl)-2,3-dihydropyridazin-3-one

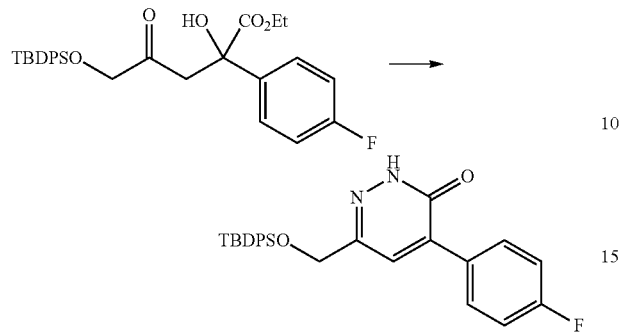

Into a 1000-mL 4-necked round-bottom flask purged and maintained with an inert atmosphere of nitrogen, was placed a solution of ethyl 5-[(tert-butyldiphenylsilyl) oxy]-2-(4-fluorophenyl)-2-hydroxy-4-oxopentanoate (292 g, 574 mmol) in acetic acid (520 mL). This was followed by the addition of hydrazine hydrate (115 g, 2.30 mol) dropwise with stirring below 30° C. in 30 min. The resulting solution was stirred for 3 h at r.t., then, heated to 80° C. for 2 hr. The reaction mixture was then poured into 2000 mL of water/ice. The resulting solution was extracted with 3×1000 of ethyl acetate and the organic layers combined. The resulting mixture was washed with 2000 mL of 5% NaHCO$_3$ and 1000 mL of brine. The mixture was dried over anhydrous sodium sulfate and concentrated under vacuum. The crude product was purified by re-crystallization from n-hexane to afford 6-[[tert-butyldiphenylsilyl)oxy]methyl]-4-(4-fluorophenyl)-2,3-dihydro pyridazin-3-one.

Step 4: 6-[[(tert-butyldiphenylsilyl)oxy]methyl]-4-(4-fluorophenyl)-2-(oxan-2-yl)-2,3-dihydro-pyridazin-3-one

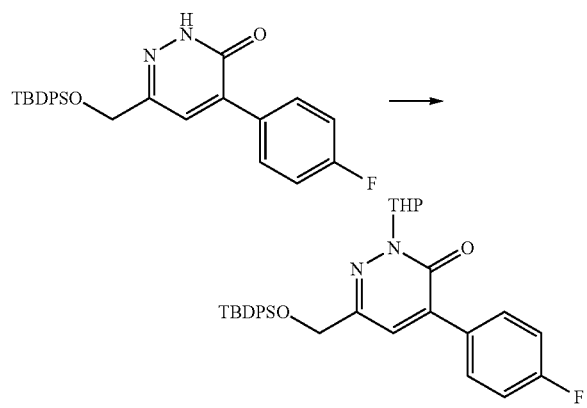

Into a 2000-mL round-bottom flask purged and maintained with an inert atmosphere of nitrogen, was placed a solution of 6-[[(tert-butyldiphenylsilyl)oxy]methyl]-4-(4-fluorophenyl)-2,3-dihydropyridazin-3-one (150 g, 327 mmol, 1.00 equiv) in toluene (1.2 L), 3,4-dihydro-2H-pyran (80 g, 951 mmol, 2.91 equiv), PPTS (15 g, 59.8 mmol, 0.18 equiv). The resulting solution was stirred for 5 h at 90° C. To this added additional DHP (55 g, 654 mmol), and the mixture was stirred overnight at 90° C. The reaction mixture was cooled to room temperature and then poured into 1000 mL of 5% NaHCO$_3$. The resulting solution was extracted with 2×500 mL of ethyl acetate and the organic layers combined. The resulting mixture was washed with 500 mL of brine. The mixture was dried over anhydrous sodium sulfate and concentrated under vacuum. This afforded (crude) 6-[[(tert-butyldiphenylsilyl)oxy]methyl]-4-(4-fluorophenyl)-2-(oxan-2-yl)-2,3-dihydropyridazin-3-one.

Step 5: 4-(4-fluorophenyl)-6-(hydroxymethyl)-2-(oxan-2-yl)-2,3-dihydropyridazin-3-one

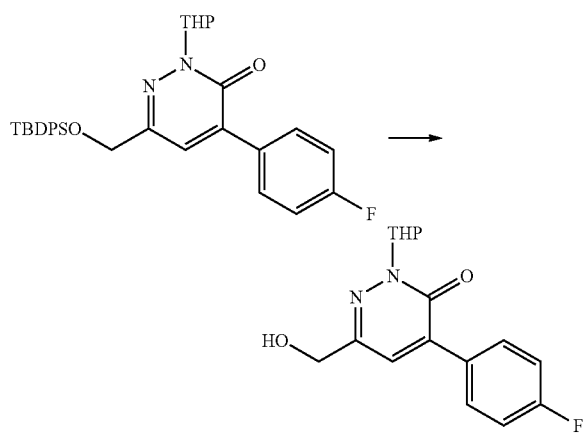

Into a 2000-mL round-bottom flask purged and maintained with an inert atmosphere of nitrogen, was placed a solution of 6-[[(tert-butyldiphenylsilyl)oxy]methyl]-4-(4-fluorophenyl)-2-(oxan-2-yl)-2,3-dihydropyridazin-3-one (220 g, 324 mmol, 1.00 equiv, 80%) in tetrahydrofuran (1.1 L). This was followed by the addition of TBAF (87 g, 333 mmol, 1.03 equiv) in several batches at 20° C. in 5 min. The resulting solution was stirred for 30 min at room temperature and then poured into 1000 mL of 5% NaHCO$_3$. The resulting solution was extracted with 2×500 mL of ethyl acetate and the organic layers combined. The resulting mixture was washed with 1000 mL of brine. The mixture was dried over anhydrous sodium sulfate and concentrated under vacuum. The residue was applied onto a silica gel column with ethyl acetate/petroleum ether (1:10-1:1) to afford 4-(4-fluorophenyl)-6-(hydroxymethyl)-2-(oxan-2-yl)-2,3-dihydro pyridazin-3-one. MS (ESI) m/z 305 (M+H)$^+$

Step 6: 6-(bromomethyl)-4-(4-fluorophenyl)-2-(tetrahydro-2H-pyran-2-yl)pyridazin-3(2H)-one

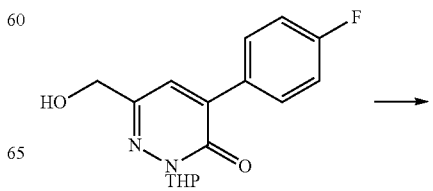

-continued

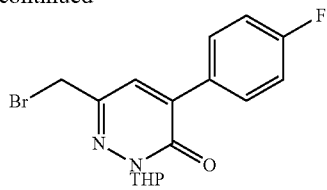

To a stirring solution of 4-(4-fluorophenyl)-6-(hydroxymethyl)-2-(tetrahydro-2H-pyran-2-yl)pyridazin-3(2H)-one (10 g, 32.9 mmol) in DCM (40 mL) at 0° C. was added carbon tetrabromide (13.08 g, 39.4 mmol) followed by a slow addition of a solution of triphenylphosphine (10.34 g, 39.4 mmol) in DCM (10 mL). The resulting mixture was allowed to stir at 0° C. for 1 hr and then concentrated under reduced pressure. Diethyl ether (500 mL) was added to the crude mixture and solids were filtered out. The filtrate was concentrated under reduced pressure and the crude product was purified by column chromatography on silica gel (ethyl acetate/hexane (0%-60%) as eluent) to afford 6-(bromomethyl)-4-(4-fluorophenyl)-2-(tetrahydro-2H-pyran-2-yl)pyridazin-3(2H)-one. MS (ESI) m/z 367, 369 (M+H)+

Step 7: 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy)benzonitrile

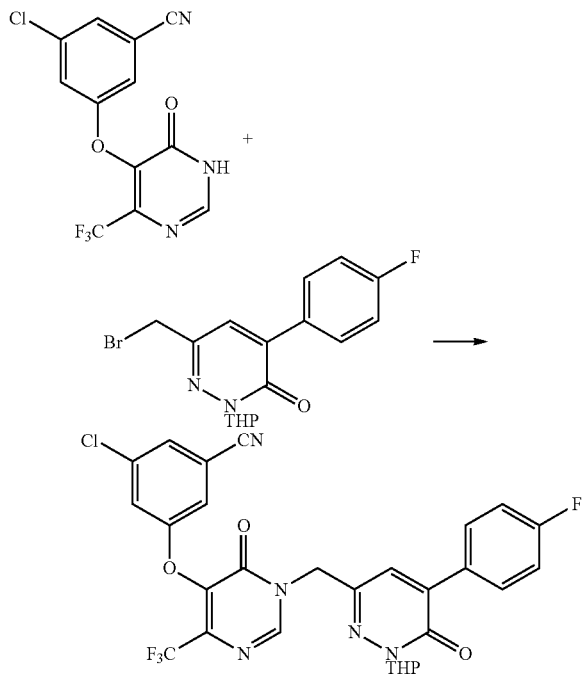

To a mixture of 6-(bromomethyl)-4-(4-fluorophenyl)-2-(tetrahydro-2H-pyran-2-yl) pyridazin-3(2H)-one (10.59 g, 28.8 mmol), and 3-chloro-5-((6-oxo-4-(trifluoromethyl)-1,6-dihydropyrimidin-5-yl)oxy)benzonitrile (9.10 g, 28.8 mmol, Example 3, step 5) in DMF (35 mL) was added DIPEA (6.55 mL, 37.5 mmol) at 0° C. After 30 min the reaction mixture was warmed up to room temperature and stirring was continued for an additional 1 hr. The mixture was concentrated under reduced pressure and water (200 mL) was added. The resulting precipitate was collected by filtration and washed with water (2×50 mL) followed by diethyl ether (3×50 mL) to afford 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy)benzonitrile. MS (ESI) m/z 601, 602 (M+H)+

Step 8: 3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile

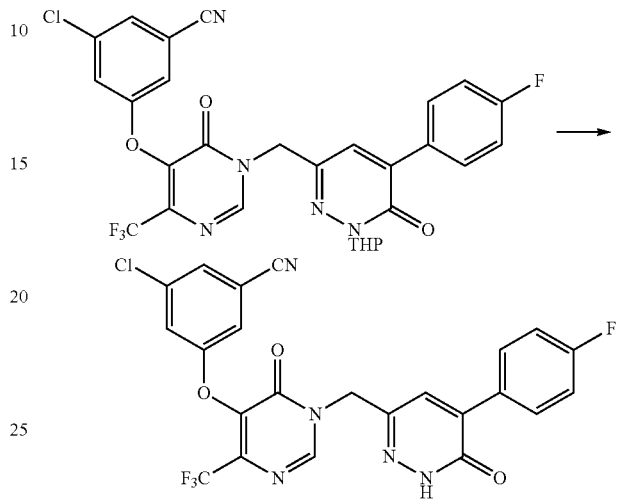

A solution of 3-chloro-5-((1-((5-(4-fluorophenyl)-6-oxo-1-(tetrahydro-2H-pyran-2-yl)-1,6-dihydropyridazin-3-yl)methyl)-6-oxo-4-(trifluoromethyl)-1,6-dihydropyrimidin-5-yl)oxy) benzonitrile (15.78 g, 26.2 mmol) in TFA (40.4 mL, 524 mmol) was stirred at r.t. for 1 hr. TFA was removed under reduced pressure and diethyl ether (250 mL) was added. The resulting solid was collected by filtration and washed with diethyl ether (2×125 mL) to afford 3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile. MS (ESI) m/z 518, 520 (M+H)+; 1H NMR: (DMSO-d6, 400 MHz) δ 13.13 (s, 1H), 8.74 (s, 1H), 7.87 (t, J=6.8 Hz, 2H), 7.62-7.72 (m, 4H), 7.26 (t, J=6.8 Hz, 2H), 5.14 (s, 2H).

Example 7

(3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl dihydrogen phosphate Step 1: di-tert-butyl ((3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl) phosphate

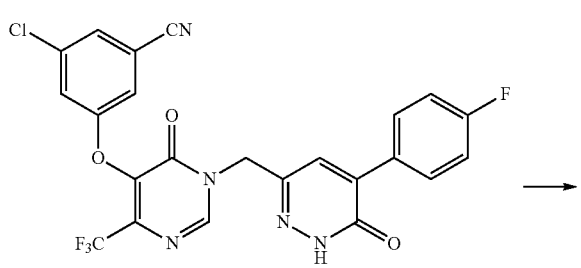

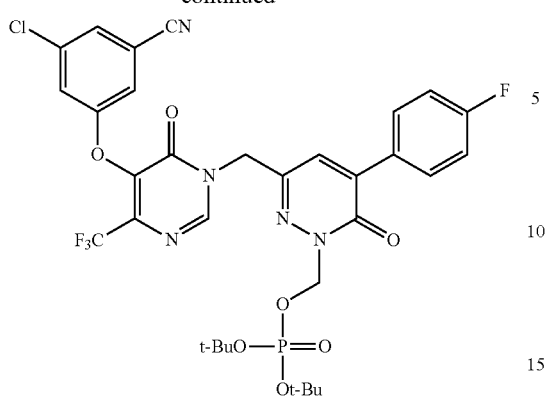

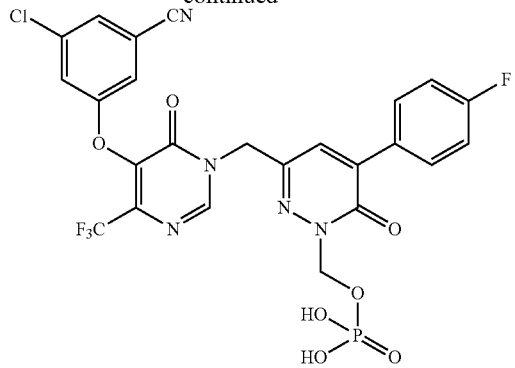

To a slurry of 3-chloro-5-((1-((5-(4-fluorophenyl)-6-oxo-1,6-dihydropyridazin-3-yl)methyl)-6-oxo-4-(trifluoromethyl)-1,6-dihydropyrimidin-5-yl)oxy)benzonitrile (250 mg, 0.48 mmol) and sodium iodide (94 mg, 0.63 mmol) in THF (3.8 mL) at 0° C. was added lithium tert-butoxide (1M in THF) (0.56 mL1, 0.56 mmol) followed by di-tert-butyl chloromethyl phosphate (0.13 mL 0.63 mmol). Reaction mixture was warmed up to room temperature and stirred further for 16 h. Upon reaction completion, it was cooled to 0° C. and quenched with a few drops of water. The solvent was removed by rotary evaporation keeping the temperature of water bath not to exceed 25° C. The residue was dissolved in DCM (25 mL) and washed with sat. NaHCO$_3$ (1×5 ml), brine (1×5 ml,) dried over anhydrous MgSO4, filtered and concentrated by rotary evaporation keeping the temperature of water bath not to exceed 25° C. to afford di-tert-butyl ((3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl) phosphate, which was used in the next step without purification.

Step 2: (3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl dihydrogen phosphate

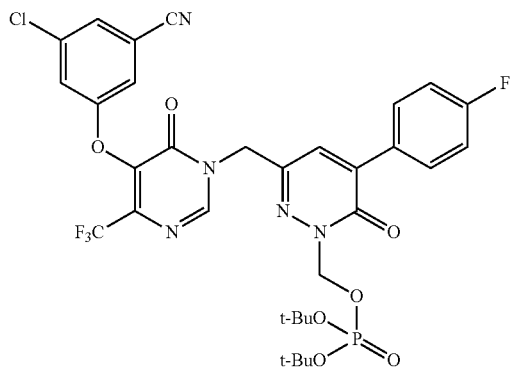

To a crude solution of di-tert-butyl ((3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl) methyl) phosphate (357 mg, 0.48 mmol) in dichloromethane (5.8 mL) at 0° C. was added trifluoroacetic acid (149 μl, 1.932 mmol). The reaction mixture was allowed to warm up to ambient temperature and stirred further for 16 h. Upon reaction completion, the mixture was filtered and purified by reverse phase HPLC (ACN/water with 0.1% TFA modifier) to afford (3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl dihydrogen phosphate. MS: 628 (M+11)$^+$ $^1$H NMR (500 MHz, DMSO-d6) δ 8.76 (s, 1H), 7.71-7.86 (m, 6H), 7.33 (t, J=8.7 Hz, 2H), 5.71 (d, J=7.7 Hz, 2H), 5.19 (s, 2H).

Intermediate H

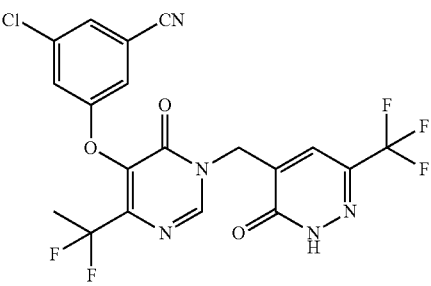 [SMILES: CC(F)(F)c1ncn(Cc2cc(C(F)(F)F)n[nH]c2=O)c(=O)c1Oc1cc(Cl)cc(C#N)c1]

3-chloro-5-((4-(1,1-difluoroethyl)-1-((6-(1,1-difluoroethyl)-3-oxo-2,3-dihydropyridazin-4-yl)methyl)-6-oxo-1,6-dihydropyrimidin-5-yl)oxy)benzonitrile Step 1: ethyl 4,4-difluoro-3-oxopentanoate

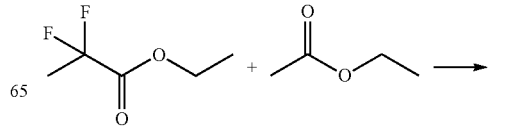

-continued

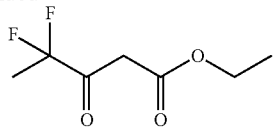

To a solution of compound ethyl 2,2-difluoropropanoate (10.6 g, 76.8 mmol) and ethyl acetate (8.11 g, 92.1 mmol, dried over MgSO$_4$) in THF (100 mL) was added LiHMDS (92 mL, 92.1 mmol) at −78° C. under N$_2$ protection. The mixture was stirred at −78° C. for 1 hour. Then the mixture was stirred at 20° C. for another 1.5 hours. The reaction was quenched with HCl solution (1 N) slowly. The mixture was extracted with EtOAc (100 mL×3), washed with brine (200 mL), dried over MgSO$_4$, filtered and concentrated under reduced pressure to give the desired product. The residue was used directly without further purification.

Step 2: 6-(1,1-difluoroethyl)pyrimidin-4(3H)-one

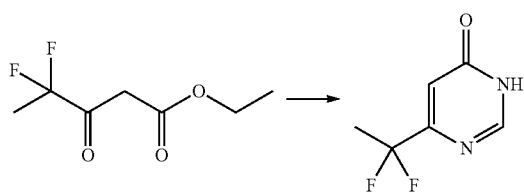

A solution of formimidamide acetate (16.0 g, 153.6 mmol) and sodium methoxide (16.6 g, 307 mmol) in methanol (140 mL) was stirred at r.t. for 20 min, then ethyl 4,4-difluoro-3-oxopentanoate (14 g crude, 76.8 mmol) was added. The resulting mixture was stirred at 70° C. for 14 hours. After cooling to room temperature, the mixture was diluted with water (200 mL), extracted with EtOAc (200 mL×3). The combined organic layers were dried over MgSO$_4$, filtered and concentrated under reduced pressure to afford the desired product. $^1$HNMR: (400 MHz, CDCl$_3$) δ 8.20 (s, 1H), 6.77 (s, 1H), 1.90 (t, J=18.8 Hz, 3H). MS (ESI) m/z 161.21 (M+H)$^+$ Step 3: 5-bromo-6-(1,1-difluoroethyl)pyrimidin-4(3H)-one

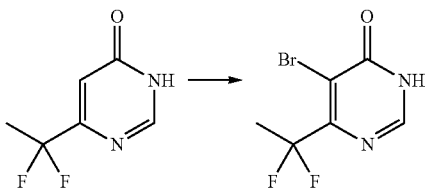

A solution of compound 6-(1,1-difluoroethyl)pyrimidin-4(3H)-one (9.5 g, 59 mmol) and potassium acetate (11.6 g, 119 mmol) in acetic acid (100 mL) was stirred at r.t. for 30 min, then Br$_2$ (11.2 g, 71 mmol) was added dropwise at r.t. The resulting mixture was stirred at reflux for 2 hours. After cooling to r.t., the mixture was quenched with Na$_2$SO$_3$ (sat.) till the color turned to light yellow, and extracted with EA (200 mL×3). The combined organic layers were dried over MgSO$_4$, filtered and concentrated under reduced pressure to afford the desired product. MS (ESI) m/z 238.8, 240.8 (M+H)$^+$.

Step 4: 5-bromo-6-(1,1-difluoroethyl)-3-(4-methoxybenzyl)pyrimidin-4(3H)-one

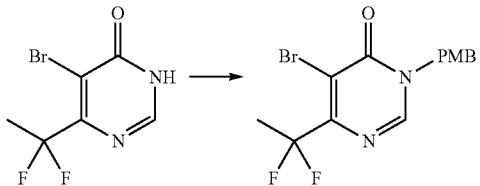

To a solution of compound 5-bromo-6-(1,1-difluoroethyl)pyrimidin-4(3H)-one (15.0 g, 59 mmol) in DMF (150 mL) was added K$_2$CO$_3$ (17.4 g, 126 mmol) and PMBCl (108. g, 69 mmol). The reaction mixture was stirred at 80° C. for 3 hours. After cooling to room temperature, the mixture was diluted with H$_2$O (100 mL) and extracted with EtOAc (200 mL×3). The combined organic layers were dried over MgSO$_4$, filtered and concentrated under reduced pressure. The residue was purified by column chromatography on silica gel (PE/EA=10/1 to 5/1) to afford the desired product. $^1$HNMR: (400 MHz, CDCl$_3$) δ 8.09 (s, 1H), 7.96 (s, 1H), 7.28 (d, 2H, J=8.4 Hz), 6.85 (s, 2H, J=8.4 Hz), 5.04 (s, 2H), 3.75 (s, 2H), 1.92 (t, J=18.4 Hz, 3H). MS (ESI) m/z 359.1, 361.1 (M+H)$^+$ Step 5: 3-chloro-5-((4-(1,1-difluoroethyl)-1-(4-methoxybenzyl)-6-oxo-1,6-dihydropyrimidin-5-yl)oxy)benzonitrile

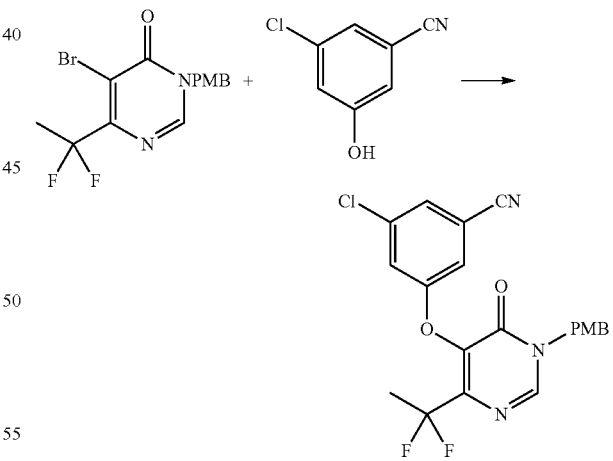

To a solution of compound 5-bromo-6-(1,1-difluoroethyl)-3-(4-methoxybenzyl)pyrimidin-4(3H)-one (3.0 g, 8.56 mmol) in NMP (50 mL) was added potassium carbonate (2.31 g, 16.70 mmol) and 3-chloro-5-hydroxybenzonitrile (3.86 g, 25.07 mmol). The mixture was heated to 140° C. for 6 hr, and then cooled down to 130° C., the mixture was stirred at 130° C. overnight. After cooling, the mixture was diluted with water (200 mL) and extracted with ethyl acetate (100 mL×3). The combined organic layers were washed with brine, dried over sodium sulfate, filtered and concentrated under reduced pressure. The residue was purified by column chromatography on silica gel (petroleum ether:ethyl acetate (20:1 to 8:1) as eluent) to give 3-chloro-5-((4-(1,1-difluoroethyl)-1-(4-methoxybenzyl)-6-oxo-1,6-dihydro pyrimidin-5-yl)oxy) benzonitrile. MS (ESI) m/z 432, 434 (M+H)⁺

Step 6: 3-chloro-5-((4-(1,1-difluoroethyl)-6-oxo-1,6-dihydropyrimidin-5-yl)oxy)benzonitrile

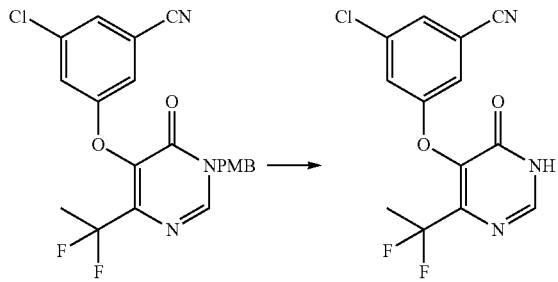

A solution of 3-chloro-5-((4-(1,1-difluoroethyl)-1-(4-methoxybenzyl)-6-oxo-1,6-dihydropyrimidin-5-yl)oxy) benzonitrile (10 g, 23.2 mmol) in mixed solvent (TFA/TFAA=48 mL/24 mL) was stirred at 100° C. for 4 hr. After cooling to room temperature, the mixture was concentrated under reduced pressure to give crude product 3-chloro-5-((4-(1,1-difluoroethyl)-6-oxo-1,6-dihydropyrimidin-5-yl)oxy)benzonitrile which was used without further purification. MS (ESI) m/z 312, 314 (M+H)⁺

Step 7: 3-(1-ethoxyvinyl)-6-methoxypyridazine

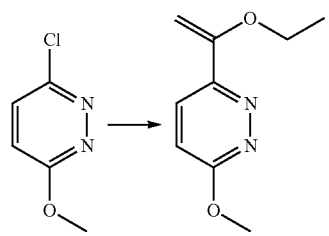

To a mixture of 3-chloro-6-methoxypyridazine (15 g, 103.8 mmol), tributyl(1-ethoxyvinyl)stannane (82.44 g, 228.3 mmol) in toluene (200 mL) was added Pd(PPh₃)₄ (6 g, 5.19 mmol) under nitrogen atmosphere. The resulting suspension was flushed three times with nitrogen and then stirred at 110° C. for 36 hr. After cooling to room temperature, the mixture was poured into ice-water, filtered through a pad of Celite®. The filtrate was extracted with ethyl acetate, and the combined organic layers were washed with brine, dried over sodium sulfate, filtered and concentrated under reduced pressure. The residue was purified by column chromatography on silica gel (petroleum ether/ethyl acetate (15:1 to 10:1) as eluent) to afford the desired product 3-(1-ethoxyvinyl)-6-methoxypyridazine. MS (ESI) m/z 181 (M+H)⁺

Step 8: 1-(6-methoxypyridazin-3-yl)ethanone

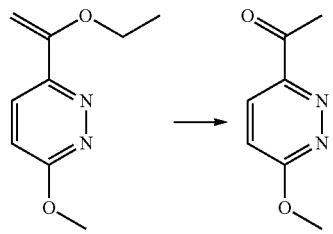

To a solution of 3-(1-ethoxyvinyl)-6-methoxypyridazine (12 g, 66.59 mmol) in 1,4-dioxane (120 mL) was added HCl/1,4-dioxane (24 mL, 4 M) dropwise at 0° C. The mixture was stirred at room temperature for 1 hr. The mixture was quenched with water and extracted with ethyl acetate. The combined organic layers were dried over anhydrous sodium sulfate, filtered and concentrated under reduced pressure. The residue was purified by column chromatography on silica gel (petroleum ether/ethyl acetate (10:1 to 8:1) as eluent) to afford 1-(6-methoxypyridazin-3-yl)ethanone. MS (ESI) m/z 153 (M+H)⁺

Step 9: 3-(1,1-difluoroethyl)-6-methoxypyridazine

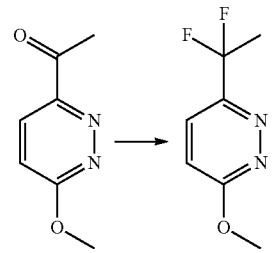

To a solution of 1-(6-methoxypyridazin-3-yl)ethanone (4.2 g, 27.6 mmol) in dichloromethane (45 mL) was added DAST (13.35 mg, 82.81 mmol) dropwise at 0° C. The mixture was stirred at 40° C. for 24 hr. After cooling to r.t., the mixture was quenched with water and extracted with ethyl acetate. The combined organic layers were dried over anhydrous sodium sulfate, filtered and concentrated under reduced pressure. The residue was purified by column chromatography on silica gel (petroleum ether/ethyl acetate (15:1 to 10:1) as eluent) to afford 3-(1,1-difluoroethyl)-6-methoxypyridazine. MS (ESI) m/z 175 (M+H)⁺

Step 10: (6-(1,1-difluoroethyl)-3-methoxypyridazin-4-yl)methanol

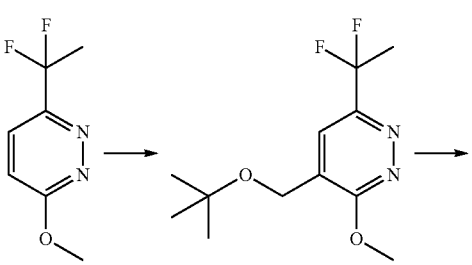

-continued

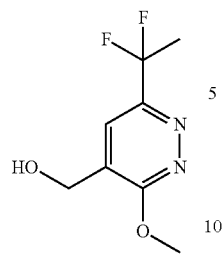

To a mixture of tert-butoxy-acetic acid (4.23 g, 32.04 mmol) in TFA/water (20 mol %, 30 mL) were added 3-(1,1-difluoroethyl)-6-methoxypyridazine (3.1 g, 17.8 mmol) and AgNO₃ (303 mg, 1.78 mmol). The mixture was flushed with nitrogen with stirring at room temperature, then the mixture was heated to 70° C., and (NH₄)₂S₂O₈ (8.12 g, 35.6 mmol) in water (40 mL) was added dropwise. After addition the mixture was stirred at 75° C. for 40 min. After cooling to room temperature, the mixture was extracted with ethyl acetate (20 mL×3), the combined organic layers were washed with brine, dried over sodium sulfate, filtered and concentrated under reduced pressure to afford crude product. A solution of 4-(tert-butoxymethyl)-6-(1,1-difluoroethyl)-3-methoxypyridazine in TFA/DCE (10 mL/40 mL) was stirred at 60° C. for 1 hr. After cooling to r.t., the mixture was concentrated under reduced pressure. The residue was dissolved in ethyl acetate (20 mL), washed with aqueous potassium carbonate, brine, dried over sodium sulfate, filtered and concentrated under reduced pressure. The residue was purified by column chromatography on silica gel (petroleum ether/ethyl acetate (8:1 to 5:1) as eluent) to afford (6-(1,1-difluoroethyl)-3-methoxy pyridazin-4-yl)methanol. MS (ESI) m/z 205 (M+H)⁺

Step 11: 4-(chloromethyl)-6-(1,1-difluoroethyl)-3-methoxypyridazine

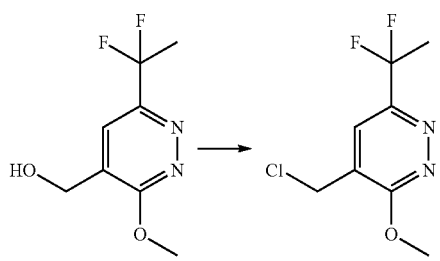

To a solution of (6-(1,1-difluoroethyl)-3-methoxypyridazin-4-yl)methanol (180 mg, 0.88 mmol) in dichloromethane (3 mL) was added triethylamine (268 mg, 2.64 mmol) and methanesulfonyl chloride (303 mg, 2.64 mmol) at 0° C. The mixture was stirred at room temperature for 24 hr, quenched with water and extracted with dichloromethane. The combined organic layers were dried over sodium sulfate, filtered and concentrated under reduced pressure. The residue was purified by preparative TLC (petroleum ether/ethyl acetate (2:1) as eluent) to afford 4-(chloromethyl)-6-(1,1-difluoroethyl)-3-methoxypyridazine. MS (ESI) m/z 223 (M+H)⁺

Step 12: 3-chloro-5-((4-(1,1-difluoroethyl)-1-((6-(1,1-difluoroethyl)-3-methoxypyridazin-4-yl)methyl)-6-oxo-1,6-dihydropyrimidin-5-yl)oxy)benzonitrile

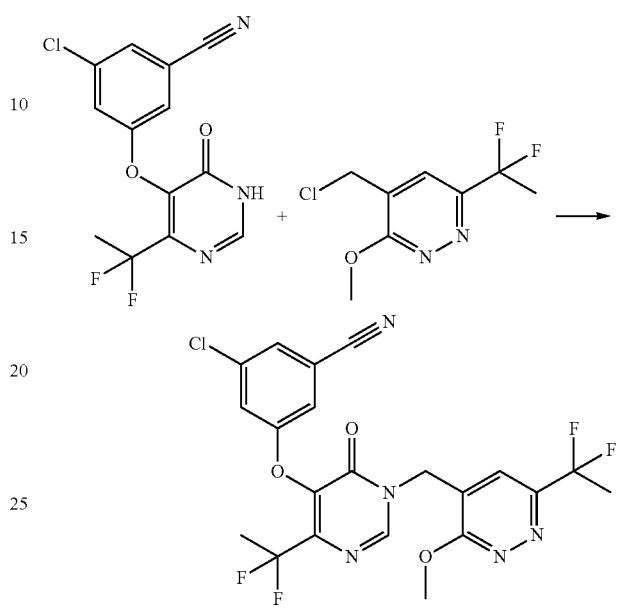

To a solution of 3-chloro-5-((4-(1,1-difluoroethyl)-6-oxo-1,6-dihydropyrimidin-5-yl)oxy)benzonitrile (500 mg, 1.60 mmol) in DMF (2 mL) was added potassium carbonate (443 mg, 3.21 mmol) and 4-(chloromethyl)-6-(1,1-difluoroethyl)-3-methoxypyridazine (as described in Steps 1-5 of Example 178) (82 mg, 0.27 mmol). The resulting mixture was stirred at 80° C. for 3 h. After cooling to room temperature, the mixture was diluted with water and extracted with EtOAc. The combined organic layers were dried over sodium sulfate, filtered, concentrated under reduced pressure. The residue was purified by preparative TLC (petroleum ether/EtOAc=1:1) to afford the desired product 3-chloro-5-((4-(1,1-difluoroethyl)-1-((6-(1,1-difluoroethyl)-3-methoxypyridazin-4-yl)methyl)-6-oxo-1,6-dihydropyrimidin-5-yl)oxy)benzonitrile. MS (ESI) m/z 498, 500 (M+H)⁺

Step 13: 3-chloro-5-((4-(1,1-difluoroethyl)-1-((6-(1,1-difluoroethyl)-3-oxo-2,3-dihydropyridazin-4-yl)methyl)-6-oxo-1,6-dihydropyrimidin-5-yl)oxy)benzonitrile

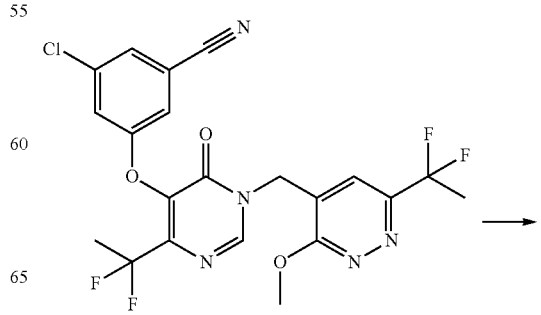

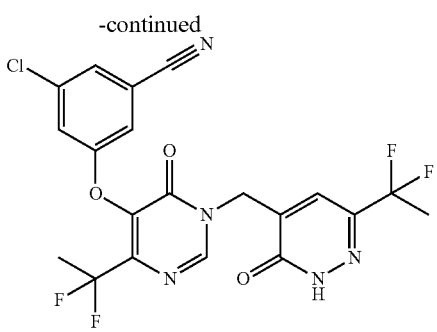

To a mixture of compound 3-chloro-5-((4-(1,1-difluoroethyl)-1-((6-(1,1-difluoroethyl)-3-methoxypyridazin-4-yl)methyl)-6-oxo-1,6-dihydropyrimidin-5-yl)oxy)benzonitrile (250 mg, 0.50 mmol) and KI (166 mg, 1.0 mmol) in acetonitrile (3 mL) was added TMSCl (109 mg, 1 mmol) at room temperature. The resulting mixture was heated and stirred at 70° C. for 1 hr. After cooling to room temperature, the mixture was diluted with EtOAc and washed with aq. $Na_2S_2O_3$ and brine, dried over anhydrous sodium sulfate and concentrated under reduced pressure. The residue was purified by preparative HPLC to afford 3-chloro-5-((4-(1,1-difluoroethyl)-1-((6-(1,1-difluoroethyl)-3-oxo-2,3-dihydropyridazin-4-yl)methyl)-6-oxo-1,6-dihydropyrimidin-5-yl)oxy)benzonitrile. $^1$H NMR (Methanol-$d_4$, 400 MHz): δ 8.60 (s, 1H), 7.68 (s, 1H), 7.47 (s, 1H), 7.28 (s, 1H), 7.24 (s, 1H), 5.07 (s, 2H), 1.92 (m, 6H). MS (ESI) m/z 484, 486 (M+H)$^+$ Example 8

(5-((5-(3-chloro-5-cyanophenoxy)-4-(1,1-difluoroethyl)-6-oxopyrimidin-1(6H)-yl)methyl)-3-(1,1-difluoroethyl)-6-oxopyridazin-1(6H)-yl)methyl dihydrogen phosphate

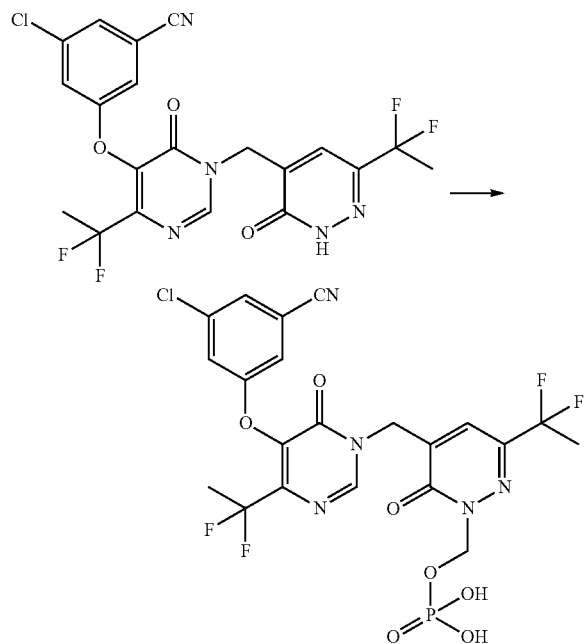

The above compound was prepared by following similar procedures as described in Example 7 steps 1-2. $^1$H NMR (500 MHz, DMSO-d6) δ 8.68 (s, 1H), 7.61-7.75 (m, 4H), 5.70 (d, J=8.2 Hz, 2H), 5.06 (s, 2H), 1.90-1.99 (m, 6H). MS: 594 (M+H)$^+$ Determination of HIV-1 Reverse Transcriptase Inhibitory Activity The heterodimeric nucleic acid substrate used in the HIV-1 RT polymerase reactions was generated by annealing the DNA primer, biotinylated pD500 (Sigma Aldrich, USA, 5'-biotin-ttg aaa tga ctg cgg tac ggc-3'), (SEQ ID NO: 1) to the nucleotide RNA template t500 (derived from hepatitis C virus [HCV] sequence, IBA, Germany, 5'-GAG GUU CAG GUG GUU UCC ACC GCA ACA CAA UCC UUC CUG GCG ACC UGC GUC AAC GGC GUG UGU UGG ACC GUU UAC CAU GGU GCU GGC UCA AAG ACC UUA GCC GGC CCA AAG GGG CCA AUC ACC CAG AUG UAC ACU AAU GUG GAC CAG GAC CUC GUC GGC UGG CAG GCG CCC CCC GGG GCG CGU UCC UUG ACA CCA UGC ACC UGU GGC AGC UCA GAC CUU UAC UUG GUC ACG AGA CAU GCU GAC GUC AUU CCG GUG CGC CGG CGG GGC GAC AGU AGG GGG AGC CUG CUC UCC CCC AGG CCU GUC UCC UAC UUG AAG GGC UCU UCG GGU GGU CCA CUG CUC UGC CCU UCG GGG CAC GCU GUG GGC AUC UUC CGG GCU GCC GUA UGC ACC CGG GGG GUU GCG AAG GCG GUG GAC UUU GUG CCC GUA GAG UCC AUG GAA ACU ACU AUG CGG UCU CCG GUC UUC ACG GAC AAC UCA UCC CCC CCG GCC GUA CCG CAG UCA UUU CAA-3'), (SEQ ID NO: 2). The HIV-1 RT wild-type enzyme (final concentration of 83 pM) was combined with an inhibitor or dimethyl sulfoxide (DMSO, 10% in the final reaction mixture) in assay buffer (62.5 mM Tris-HCl [pH 7.8], 1.25 mM dithiothreitol, 7.5 mM $MgCl_2$, 100 mM KCl, 0.03% CHAPS, and 125 μM EGTA). The mixture was then preincubated on an orbital shaker for 30 min at room temperature in microtiter plates (Costar 3365, Corning, USA). A polymerization reaction was initiated by the addition of RNA template/pD500 DNA primer hybrid (16.6 nM final of RNA/DNA hybrid) and dNTPs (2 μM dATP, dGTP, dCTP and 66.6 nM Ru-dUTP (Meso Scale Discovery, USA)). Plate was sealed and incubated for 5-10 min at room temperature on an orbital shaker. Plate was then incubated for 90 min at 37° C. and reactions quenched with 60 μl quenching buffer (50 mM EDTA, 0.7% BSA, 0.7% Tween-20, 0.017% sodium azide in PBS). The resulting solution was incubated at room temperature for an additional 5 min and then 50 μL was transferred to pre-blocked Avidin plates (L15AA, Meso Scale Discovery). Each well of Avidin plate was blocked for 1 h at room temperature with 100 μL 5% BSA in PBS. Blocking solution was removed by tapping vigorously on filter paper to remove all excess liquid. Reaction on pre-blocked avidin plate proceeded for 60 min at room temperature and then contents removed by tapping vigorously on filter paper to remove all excess liquid. After washing plate 3 times with 150 μL 1×PBS and blotting dry between cycles, 150 μL 1× Read Buffer T (4× Read Buffer T, Meso Scale Discovery) was added and incubated for 5 min at room temperature before counting on a Sector Imager 56000 (Meso Scale Discovery). Titration curves and $IC_{50}$ values were calculated using a four parameter logistic fit according to standard procedures. Briefly, % Inhibition=100×((sample raw value)−(mean value of the low control or 0% inhibition))/((mean value of wells representing 100% inhibition)−(mean value of 0% inhibition)). In this assay, low control wells contain DMSO (0% inhibition) and 100% inhibition wells contain 1 μM efavirenz.

The results of compounds of the invention tested in the above assay are shown in the following Table 2.

TABLE 2

| Parent Compound of: | $IC_{50}$ (nM) |
|---|---|
| Example No 1 | 6.0 |
| Example No 2 | 3.3 |
| Example No 3 | 2.7 |
| Example No 4 | 3.2 |
| Example No 5 | 4.6 |
| Example No 6 | 7.9 |
| Example No 7 | 3.7 |
| Example No 8 | 4.7 |

Pharmacokinetic Studies

All animal studies were carried out under Good Laboratory Practice regulations for nonclinical laboratory studies. All animal housing and care procedures were in compliance with the Federal Animal Welfare Act and the Institute for Laboratory Animal Resources. All procedures carried out on the animals were reviewed and approved by the Institutional Animal Care and Use Committee. The animal facility was fully accredited with the Association for Assessment and Accreditation of Laboratory Animal Care International.

Two or three male Wistar-Hannover rats weighing 250 to 350 grams with vendor-placed carotid artery catheters were obtained from Charles River (Raleigh, N.C., U.S.A.). Animals were acclimated on a 12-hour light:dark cycle for a minimum of three days in ventilated plastic cages with food and water ad libitum. Blood samples were automatically collected using the Instech Automated Blood sampler (ABS, Plymouth Meeting, Pa.) at designated intervals up to 24 hr and were manually collected post 24 hr.

Animals were fasted overnight before either the Parent compounds of Examples 1-8 (Formula I') or compounds of Examples 1 to 8 (Formula I) were administered to rats via an oral gavage at the doses and in vehicles specified in Table 3. The animals were allowed access to water ad libitum, while food was returned 4 hours after dosing.

Blood was drawn from catheters placed in the carotid vein at pre-dose, and 0.25, 0.5, 1, 2, 4, 8, 12, 18, 24, 30, and 48 hr after dosing for all compounds and additionally at 72 hr for compounds of example 1, 3, 4, 5, and 7. The plasma was separated by centrifugation (2 minutes at 10000 rpm) and stored at −70° C. until further analysis.

The quantitative analysis of the compounds was performed using a liquid chromatography and tandem mass spectrometry method (LC-MS/MS). The plasma samples were stabilized as needed prior to extraction. Fifty microliter of each unknown together with the standards and quality control samples were extracted using an automated protein precipitation procedure on a Hamilton workstation. The extract was centrifuged and the supernatant was transferred for analysis. The separation was enabled by a Thermo Aria LX-2 LC system on a reversed phase column e g Waters XSelect HSS T3 XP (50×2.1 mm×2.5 u) or Phenomenex Beta Test Column (50×2.1 mm). The compounds were detected using selected reaction monitoring (SRM) methods by an AB Sciex API5000 mass spectrometer in the positive or negative ionization mode. In addition, chromatographic peaks for Parent compounds of Examples 1-8 (Formula I') and compounds of Examples 1 to 8 (Formula I) were resolved chromatographically with baseline to baseline separation.

Pharmacokinetic parameters were obtained using non-compartmental methods (Watson®). The area under the plasma concentration-time curve ($AUC_{0-t}$) was calculated from the first time point (0 minutes) up to the last time point with measurable drug concentration (i.e., concentration of Parent (Formula I' compound) resulting after administration of each of the Parent and Example compounds) using the linear trapezoidal or linear/log-linear trapezoidal rule. The remaining area under the plasma concentration-time curve ($AUC_{t-\infty}$) was estimated by dividing the observed concentration at the last time point by the elimination rate constant. This value was added to $AUC_{0-t}$ to estimate the $AUC_{0-\infty}$. The maximum plasma concentration ($C_{max}$) and the time at which maximum concentration occurred ($T_{max}$) were obtained by inspection of the plasma concentration-time data.

Table 3 provides AUC values obtained in these studies. In Table 3, the Parent of each Example number refers to the Parent counterpart compound of said Example number compound wherein $R^4$ is replaced with —H.

TABLE 3

Results of PK Studies

| | Dose | Rat $AUC_{(0-\infty)}$ | Vehicle |
|---|---|---|---|
| Ex. 1 | 6.2 mg/kg PO | 14.3 µM · hr | 0.5% methylcellulose |
| Parent of Ex. 2 | 5 mg/kg PO | 15.3 µM · hr | 40% PEG400/10% Tween-80/50% water |
| Ex. 2 | 6.25 mg/kg PO | 16.0 µM · hr | 0.5% methylcellulose |
| Parent of Ex. 3 | 5 mg/kg PO | 10.2 µM · hr | 40% PEG400/10% Tween-80/50% water |
| Ex. 3 | 6.2 mg/kg PO | 14.0 µM · hr | 0.5% methylcellulose |
| Parent of Ex. 4 | 5 mg/kg PO | 21.0 µM · hr | 40% PEG400/10% Tween-80/50% water |
| Ex. 4 | 6.2 mg/kg PO | 15.0 µM · hr | 0.5% methylcellulose |
| Parent of Ex. 5 | 5 mg/kg PO | 29.1 µM · hr | 40% PEG400/10% Tween-80/50% water |
| Ex. 5 | 6.2 mg/kg PO | 28.2 µM · hr | 0.5% methylcellulose |
| Parent of Ex. 6 | 5 mg/kg PO | 2.0 µM · hr | 40% PEG400/10% Tween-80/50% water |
| Ex. 6 | 6.6 mg/kg PO | 5.7 µM · hr | 40% PEG400/10% Tween-80/50% water |
| Parent of Ex. 7 | 5 mg/kg PO | 8.2 µM · hr | 40% PEG400/10% Tween-80/50% water |
| Ex. 7 | 6.2 mg/kg PO | 11.6 µM · hr | 0.5% methylcellulose |
| Parent of Ex. 8 | 5 mg/kg PO | 13.9 µM · hr | 40% PEG400/10% Tween-80/50% water |
| Ex. 8 | 5 mg/kg PO | 21.6 µM · hr | 0.5% methylcellulose |

While the foregoing specification teaches the principles of the present invention, with examples provided for the purpose of illustration, the practice of the invention encompasses all of the usual variations, adaptations and/or modifications that come within the scope of the following claims. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All publications, patents and patent applications cited herein are incorporated by reference in their entirety into the disclosure.

wherein $R^1$ is

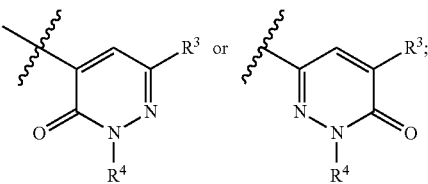

$R^2$ is halo or —$C_{1-3}$ alkyl substituted with 1 to 3 of —F;
$R^3$ is (a) halo, (b) —$C_{1-3}$ alkyl substituted with 1 to 3 of —F, or (3) phenyl substituted with halo; and

---

---

What is claimed is:

1. A compound of structural Formula I or a pharmaceutically acceptable salt thereof:

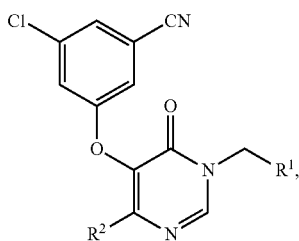

I $R^4$ is

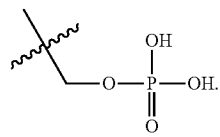 [SMILES: *COP(=O)(O)O]

2. The compound of claim 1 or a pharmaceutically acceptable salt thereof, wherein $R^1$ is 3. The compound of claim 1 or a pharmaceutically acceptable salt thereof, wherein $R^1$ is

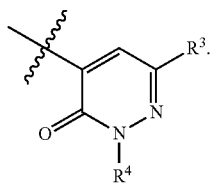

4. The compound of claim 1, or a pharmaceutically acceptable salt thereof, wherein $R^2$ is methyl substituted with 1, 2 or 3 of —F; or ethyl substituted with 1, 2 or 3 of —F.

5. The compound of claim 4, or a pharmaceutically acceptable salt thereof, wherein $R^2$ is —$CHF_2$, —$CF_3$, or —$CF_2CH_3$.

6. The compound of claim 1, or a pharmaceutically acceptable salt thereof, wherein $R^3$ is —F; —Cl; methyl substituted with 1, 2 or 3 of —F; ethyl substituted with 1, 2 or 3 of —F; or phenyl substituted with —F.

7. The compound of claim 6, or a pharmaceutically acceptable salt thereof, wherein $R^3$ is —Cl, —$CHF_2$, —$CF_3$, —$CF_2CH_3$, or phenyl substituted with —F.

8. The compound of claim 1, or a pharmaceutically acceptable salt thereof, wherein $R^4$ is:

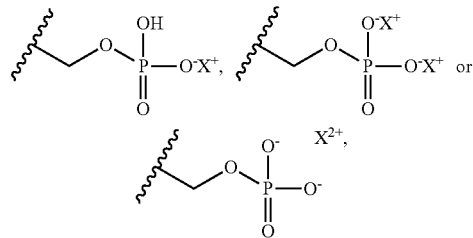

wherein $X^+$ and $X^{2+}$ are positive counter-ions.

9. The compound of claim 1 that is:

10. A pharmaceutical composition comprising an effective amount of the compound of claim 9 or a pharmaceutically acceptable salt thereof and a pharmaceutically acceptable carrier.

11. The pharmaceutical composition of claim 10, further comprising an effective amount of an anti-HIV agent selected from an HIV antiviral agent, an immunomodulator, or anti-infective agent.

12. The pharmaceutical composition of claim 10, further comprising an effective amount of an HIV protease inhibitor, HIV reverse transcriptase inhibitor, HIV integrase inhibitor, HIV fusion inhibitor, HIV entry inhibitor, or HIV maturation inhibitor.

13. A method for the inhibition of HIV replication in a subject in need thereof, which comprises administering to the subject an effective amount of the compound of claim 1 or a pharmaceutically acceptable salt thereof.

14. A method for the treatment of infection by HIV or for the treatment or delay in the onset of AIDS in a subject in need thereof, which comprises administering to the subject an effective amount of the compound of claim 1 or a pharmaceutically acceptable salt thereof.

15. The method of claim 14 wherein the subject is human.

16. The method of claim 15 further comprising administering an effective amount of an anti-HIV agent selected from an HIV antiviral agent, an immunomodulator, or anti-infective agent.

17. The method of claim 15 further comprising administering an effective amount of an HIV protease inhibitor, HIV reverse transcriptase inhibitor, HIV integrase inhibitor, HIV fusion inhibitor, HIV entry inhibitor, or HIV maturation inhibitor.

18. The method of claim 15 further comprising administering an effective amount of one or more additional anti-HIV agents selected from: abacavir, abacavir sulfate, abacavir+lamivudine, abacavir+lamivudine+zidovudine, amprenavir, atazanavir, atazanavir sulfate, AZT, capravirine, darunavir, ddC, ddI, delavirdine, delavirdine mesylate, dolutegravir, doravirine, efavirenz, efavirenz+emtricitabine+tenofovir DF, 4'-ethynyl-2-fluoro-2'-deoxyadenosine, elvitegravir, emtricitabine, emtricitabine+tenofovir DF, emivirine, enfuvirtide, enteric coated didanosine, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tipranavir and vicriviroc.

1) (5-((5-(3-chloro-5-cyanophenoxy)-4-(difluoromethyl)-6-oxopyrimidin-1(6H)-yl)methyl)-3-(difluoromethyl)-6-oxopyridazin-1(6H)-yl)methyl dihydrogen phosphate;
2) (3-chloro-5-((5-(3-chloro-5-cyanophenoxy)-4-(difluoromethyl)-6-oxopyrimidin-1(6H)-yl)methyl)-6-oxopyridazin-1(6H)-yl)methyl dihydrogen phosphate;
3) 3-chloro-5-((5-(3-chloro-5-cyanophenoxy)-6-oxo-4-(trifluoromethyl)pyrimidin-1(6H)-yl)methyl)-6-oxopyridazin-1(6H)-yl)methyl dihydrogen phosphate;
4) (5-((5-(3-chloro-5-cyanophenoxy)-6-oxo-4-(trifluoromethyl)pyrimidin-1(6H)-yl)methyl)-3-(difluoromethyl)-6-oxopyridazin-1(6H)-yl)methyl dihydrogen phosphate;
5) (5-((5-(3-chloro-5-cyanophenoxy)-6-oxo-4-(trifluoromethyl)pyrimidin-1(6H)-yl)methyl)-3-(1,1-difluoroethyl)-6-oxopyridazin-1(6H)-yl)methyl dihydrogen phosphate;
6) (3-((5-(3-chloro-5-cyanophenoxy)-6-oxo-4-(trifluoromethyl)pyrimidin-1(6H)-yl)methyl)-6-oxo-5-(trifluoromethyl)pyridazin-1(6H)-yl)methyl dihydrogen phosphate;
7) (3-((5-(3-chloro-5-cyanophenoxy)-6-oxo-4-(trifluoromethyl)pyrimidin-1(6H)-yl)methyl)-5-(4-fluorophenyl)-6-oxopyridazin-1(6H)-yl)methyl dihydrogen phosphate; or
8) (5-((5-(3-chloro-5-cyanophenoxy)-4-(1,1-difluoroethyl)-6-oxopyrimidin-1(6H)-yl)methyl)-3-(1,1-difluoroethyl)-6-oxopyridazin-1(6H)-yl)methyl dihydrogen phosphate;

or a pharmaceutically acceptable salt thereof.

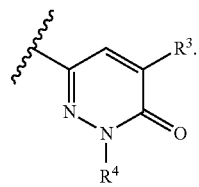

19. The pharmaceutical composition of claim 10 further comprising an effective amount of one or more additional anti-HIV agents selected from: abacavir, abacavir sulfate, abacavir+lamivudine, abacavir+lamivudine+zidovudine, amprenavir, atazanavir, atazanavir sulfate, AZT, capravirine, darunavir, ddC, ddI, delavirdine, delavirdine mesylate, dolutegravir, doravirine, efavirenz, efavirenz+emtricitabine+tenofovir DF, 4'-ethynyl-2-fluoro-2'-deoxyadenosine, elvitegravir, emtricitabine, emtricitabine+tenofovir DF, emivirine, enfuvirtide, enteric coated didanosine, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tenofovir disoproxil fumarate, tenofovir hexadecyloxypropyl, tipranavir and vicriviroc.

20. The compound of claim 1 selected from:

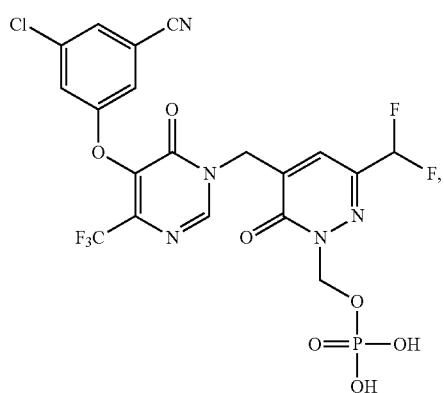

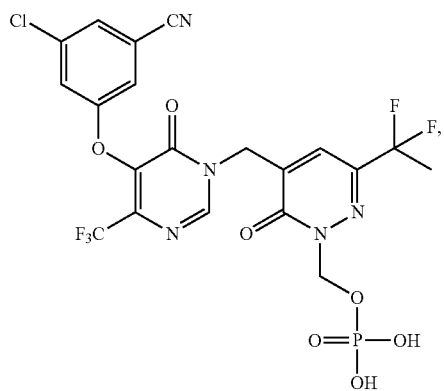

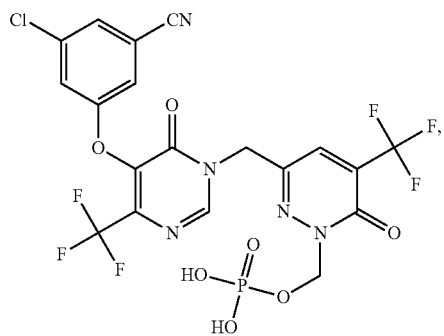

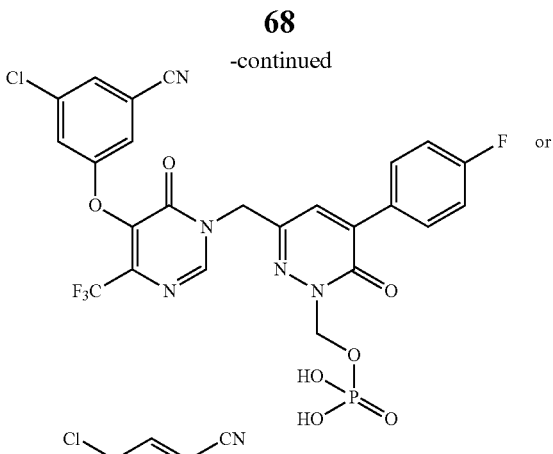

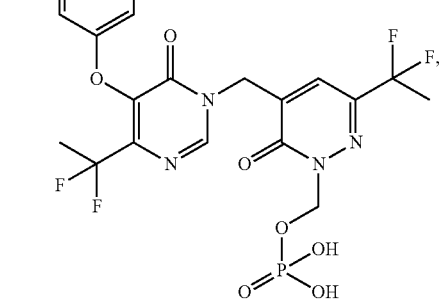

or a pharmaceutically acceptable salt thereof.

21. A compound that is:

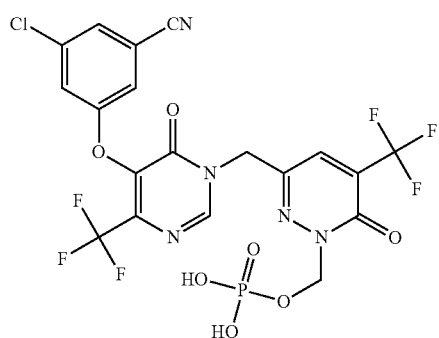 [SMILES: N#Cc1cc(Cl)cc(Oc2c(C(F)(F)F)ncn(Cc3cc(C(F)(F)F)c(=O)n(COP(=O)(O)O)n3)c2=O)c1]

or a compound that is a pharmaceutically acceptable salt thereof.

22. The compound of claim 21 that is a pharmaceutically acceptable salt of:

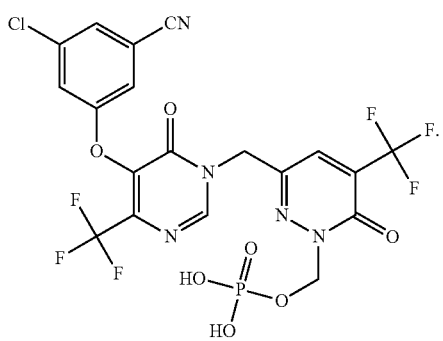 [SMILES: N#Cc1cc(Cl)cc(Oc2c(C(F)(F)F)ncn(Cc3cc(C(F)(F)F)c(=O)n(COP(=O)(O)O)n3)c2=O)c1]

23. The compound of claim 21 that is:

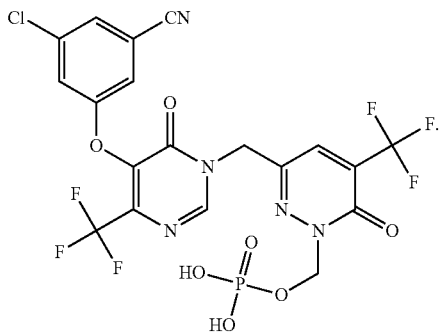 [SMILES: N#Cc1cc(Cl)cc(Oc2c(C(F)(F)F)ncn(Cc3cc(C(F)(F)F)c(=O)n(COP(=O)(O)O)n3)c2=O)c1]

24. A pharmaceutical composition comprising an effective amount of the compound of claim 21 and a pharmaceutically acceptable carrier.

25. The pharmaceutical composition of claim 24 further comprising an effective amount of an anti-HIV agent selected from an HIV antiviral agent, an immunomodulator, or anti-infective agent.

26. The pharmaceutical composition of claim 24 further comprising an effective amount of an HIV protease inhibitor, HIV reverse transcriptase inhibitor, HIV integrase inhibitor, HIV fusion inhibitor, HIV entry inhibitor, or HIV maturation inhibitor.

27. The pharmaceutical composition of claim 24 further comprising an effective amount of one or more additional anti-HIV agents selected from: abacavir, abacavir sulfate, abacavir+lamivudine, abacavir+lamivudine+zidovudine, amprenavir, atazanavir, atazanavir sulfate, AZT, capravirine, darunavir, ddC, ddI, delavirdine, delavirdine mesylate, dolutegravir, doravirine, efavirenz, efavirenz+emtricitabine+tenofovir DF, 4'-ethynyl-2-fluoro-2'-deoxyadenosine, elvitegravir, emtricitabine, emtricitabine+tenofovir DF, emivirine, enfuvirtide, enteric coated didanosine, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tenofovir disoproxil fumarate, tenofovir hexadecyloxypropyl, tipranavir and vicriviroc.

28. A method for the treatment of infection by HIV or for the treatment or delay in the onset of AIDS in a subject in need thereof, which comprises administering to the subject an effective amount of the compound of claim 21.

29. The method of claim 28 wherein the subject is human.

30. The method of claim 29 further comprising administering an effective amount of an anti-HIV agent selected from an HIV antiviral agent, an immunomodulator, or anti-infective agent.

31. The method of claim 29 further comprising administering an effective amount of an HIV protease inhibitor, HIV reverse transcriptase inhibitor, HIV integrase inhibitor, HIV fusion inhibitor, HIV entry inhibitor, or HIV maturation inhibitor.

32. The method of claim 29 further comprising administering an effective amount of one or more additional anti-HIV agents selected from: abacavir, abacavir sulfate, abacavir+lamivudine, abacavir+lamivudine+zidovudine, amprenavir, atazanavir, atazanavir sulfate, AZT, capravirine, darunavir, ddC, ddI, delavirdine, delavirdine mesylate, dolutegravir, doravirine, efavirenz, efavirenz+emtricitabine+tenofovir DF, 4'-ethynyl-2-fluoro-2'-deoxyadenosine, elvitegravir, emtricitabine, emtricitabine+tenofovir DF, emivirine, enfuvirtide, enteric coated didanosine, etravirine, fosamprenavir calcium, indinavir, indinavir sulfate, lamivudine, lamivudine+zidovudine, lopinavir, lopinavir+ritonavir, maraviroc, nelfinavir, nelfinavir mesylate, nevirapine, PPL-100, raltegravir, rilpivirine, ritonavir, saquinavir, saquinavir mesylate, stavudine, tipranavir and vicriviroc.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Chemically synthesized

<400> SEQUENCE: 1
ttgaaatgac tgcggtacgg c                                          21

<210> SEQ ID NO 2
<211> LENGTH: 501
<212> TYPE: RNA
<213> ORGANISM: Artificial Sequence
<220> FEATURE:
<223> OTHER INFORMATION: Chemically synthesized

<400> SEQUENCE: 2
gagguucagg ugguuuccac cgcaacacaa uccuuccugg cgaccugcgu caacggcgug     60
uguuggaccg uuuaccaugg ugcuggcuca aagaccuuag ccggcccaaa ggggccaauc    120
acccagaugu acacuaaugu ggaccaggac cucgucggcu ggcaggcgcc ccccggggcg    180
cguuccuuga caccaugcac cuguggcagc ucagaccuuu acuuggucac gagacaugcu    240
gacgucauuc cggugcgccg gcggggcgac aguaggggga gccugcucuc ccccaggccu    300
gucuccuacu ugaagggcuc uucggguggu ccacugcucu gcccuucggg gcacgcugug    360
ggcaucuucc gggcugccgu augcacccgg gggguugcga aggcggugga cuuugugccc    420
guagagucca uggaaacuac uaugcggucu ccggucuuca cggacaacuc auccccccg     480 gccguaccgc agucauuuca a                                             501